United States Patent
Swoboda et al.

(10) Patent No.: US 11,530,378 B2
(45) Date of Patent: Dec. 20, 2022

(54) NANOSTRAW WELL INSERT DEVICES FOR IMPROVED CELL TRANSFECTION AND VIABILITY

(71) Applicant: THE BOARD OF TRUSTEES OF THE LELAND STANFORD JUNIOR UNIVERSITY, Stanford, CA (US)

(72) Inventors: Ryan T. Swoboda, Orange Park, FL (US); Yuhong Cao, Palo Alto, CA (US); Sergio Leal-Ortiz, Stanford, CA (US); Stefanie Rothkoetter, Stanford, CA (US); Nicholas A. Melosh, Menlo Park, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 1045 days.

(21) Appl. No.: 16/302,364

(22) PCT Filed: Jun. 9, 2017

(86) PCT No.: PCT/US2017/036806
§ 371 (c)(1),
(2) Date: Nov. 16, 2018

(87) PCT Pub. No.: WO2017/214541
PCT Pub. Date: Dec. 14, 2017

(65) Prior Publication Data
US 2019/0367861 A1    Dec. 5, 2019

Related U.S. Application Data

(60) Provisional application No. 62/347,928, filed on Jun. 9, 2016.

(51) Int. Cl.
*C12M 1/00*    (2006.01)
*B01L 3/00*    (2006.01)
(Continued)

(52) U.S. Cl.
CPC ............. *C12M 29/16* (2013.01); *B01L 3/508* (2013.01); *C12M 25/02* (2013.01); *C12M 25/10* (2013.01);
(Continued)

(58) Field of Classification Search
CPC .. C12N 2539/00; C12N 5/0075; C12M 29/16; C12M 25/10; B01L 3/508;
(Continued)

(56) References Cited

U.S. PATENT DOCUMENTS 6,368,851 B1    4/2002    Baumann et al.
7,152,616 B2    12/2006    Zucchelli et al.
(Continued)

FOREIGN PATENT DOCUMENTS

CN        1286716 C        11/2006
CN        102656260 A       9/2012
(Continued)

OTHER PUBLICATIONS

Sharei et al.; Ex Vivo Cytosolic Delivery of Functional Macromolecules to Immune Cells; PloS One; 10(4); e0118803, 12 pages; Jan. 7, 2015.
(Continued)

*Primary Examiner* — Brian J. Sines

(57) ABSTRACT

Described herein are nanostraw well insert apparatuses (e.g., devices and systems) that include nanotubes extending through and out of a membrane so that a material can pass through the membrane from a fluid reservoir depot and into a cell grown onto the nanotubes when electrical energy (e.g., electroporation energy) is applied. In particular, the device, systems and methods described herein may be adapted for cell growth viability and transfection efficiency (e.g., >70%). These apparatuses may be readily integratable into
(Continued)

cell culturing processes for improved transfection efficiency, intracellular transport, and cell viability.

26 Claims, 14 Drawing Sheets

(51) Int. Cl.
    *C12M 1/12*         (2006.01)
    *C12N 5/00*         (2006.01)
    *C23C 16/40*        (2006.01)
    *C23C 16/455*      (2006.01)
    *C23C 16/56*        (2006.01)

(52) U.S. Cl.
    CPC .......... *C12N 5/0075* (2013.01); *C23C 16/402* (2013.01); *C23C 16/403* (2013.01); *C23C 16/405* (2013.01); *C23C 16/45553* (2013.01); *C23C 16/45555* (2013.01); *C23C 16/56* (2013.01); *B01L 2300/0609* (2013.01); *B01L 2300/0672* (2013.01); *B01L 2300/0832* (2013.01); *B01L 2300/12* (2013.01); *B01L 2400/0415* (2013.01); *C12N 2531/00* (2013.01); *C12N 2533/00* (2013.01); *C12N 2539/00* (2013.01)

(58) Field of Classification Search
    CPC ..... B01L 2300/0609; B01L 2300/0832; B01L 2400/0415
    See application file for complete search history.

(56) References Cited

U.S. PATENT DOCUMENTS

| | | | |
|---|---|---|---|
| 7,160,532 | B2 | 1/2007 | Liu et al. |
| 8,808,516 | B2 | 8/2014 | Melosh et al. |
| 9,266,725 | B2 * | 2/2016 | VanDersarl .............. B82Y 5/00 |
| 9,304,132 | B2 | 4/2016 | Park et al. |
| 9,856,448 | B2 | 1/2018 | Melosh et al. |
| 10,150,947 | B2 | 12/2018 | Vandersarl et al. |
| 2004/0182707 | A1 | 9/2004 | Jardemark et al. |
| 2006/0213259 | A1 | 9/2006 | Prinz et al. |
| 2007/0100086 | A1 | 5/2007 | Hong et al. |
| 2008/0302960 | A1 | 12/2008 | Meister et al. |
| 2009/0220561 | A1 | 9/2009 | Jin et al. |
| 2010/0035322 | A1 | 2/2010 | Raffa et al. |
| 2010/0140111 | A1 | 6/2010 | Gimsa et al. |
| 2010/0215724 | A1 | 8/2010 | Prakash et al. |
| 2011/0168968 | A1 | 7/2011 | Yang et al. |
| 2011/0208031 | A1 | 8/2011 | Wolfe et al. |
| 2012/0040370 | A1 | 2/2012 | Orwar et al. |
| 2012/0225435 | A1 | 9/2012 | Seger et al. |
| 2012/0264108 | A1 | 10/2012 | Chen et al. |
| 2013/0118621 | A1 | 5/2013 | Weber et al. |
| 2014/0342445 | A1 | 11/2014 | Ingber et al. |
| 2015/0197807 | A1 | 7/2015 | Park et al. |
| 2016/0032275 | A1 | 2/2016 | Actis et al. |
| 2018/0273978 | A1 * | 9/2018 | Dickerson ............ C12N 5/0075 |
| 2019/0119629 | A1 | 4/2019 | Vandersarl et al. |
| 2019/0359974 | A1 | 11/2019 | Melosh et al. |
| 2019/0365803 | A1 | 12/2019 | Melosh et al. |

FOREIGN PATENT DOCUMENTS

| | | |
|---|---|---|
| JP | 11346764 A | 12/1999 |
| JP | 2003501639 A | 1/2003 |
| JP | 2003505073 A | 2/2003 |
| JP | 2009541198 A | 11/2009 |
| WO | WO2002/058847 A2 | 8/2002 |
| WO | WO2009/063776 A1 | 3/2011 |
| WO | WO2017/027549 A1 | 2/2017 |
| WO | WO2017/214541 A1 | 12/2017 |
| WO | WO2018/053020 A1 | 3/2018 |

OTHER PUBLICATIONS

Sip et al., Microfluidic transwell inserts for generation of tissue culture-friendly gradients in well plates; Lab on a Chip, 14(2); pp. 302-314; (year of pub. sufficiently earlier than effective US filing date and any foreign priority date); 2014.

Xie et al.; Nanostraw-Electroportation System for Highly Efficient Intracellular Delivery and Transfection; ACS Nano; 7(5); pp. 4351-4358; Apr. 18, 2013.

Baek et al.; Gene transfection for stem cell therapy; Current Stem Cell Reports; 2(1); pp. 52-61; Jan. 27, 2016.

Schmiderer et al.; Efficient and nontoxic biomolecule delivery to primary human hematopoietic stem cells using nanostraws; Proceedings of the National Academy of Sciences; 117(35); pp. 21267-21273; Sep. 2020.

Hjort et al.; U.S. Appl. No. 17/081,983 entitled "Apparatuses and methods using nanostraws to deliver biologically relevant cargo into non-adherent cells," filed Oct. 27, 2020.

Abhyankar et al.; Characterization of a membrane-based gradient generator for use in cell-signaling studies; Lab Chip; 6(3):389-393; Mar. 2006.

Actis et al.; Compartmental genomics in living cells revealed by single-cell nanobiopsy; ACS Nano; 8(1); pp. 546-553; Jan. 28, 2014.

Adler et al.; Emerging links between surface nanotechnology and endocytosis: impact on nonviral gene delivery; Nano Today; 5(6):553-569; Dec. 2010 (author manuscript, 15 pgs.).

Ainslie et al.; Microfabricated devices for enhanced bioadhesive drug delivery: attachment to and small-molecule release through a cell monolayer under flow; Small; 5(24):2857-2863; Dec. 2009.

Almquist et al.; Fusion of biomimetic stealth probes into lipid bilayer cores; Proc Natl Acad Sci U S A.; 107(13):5815-5820; Mar. 2010.

Almquist et al.; Nanoscale patterning controls inorganic-membrane interface structure; Nanoscale; 3(2):391-400; Feb. 2011.

Bancroft et al.; Fluid flow increases mineralized matrix deposition in 3D perfusion culture of marrow stromal osteoblasts in a dose-dependent manner; PNAS; 99(20): 12600-12605; Oct. 1, 2002.

Bernards et al.; Nanoscale porosity in polymer films; fabrication and therapeutic applications; Soft Matter; 6(8):1621-1631; Jan. 2010 (author manuscript, 13 pgs.).

Black et al.; Upregulation of a silent sodium channel after peripheral, not not central, nerve injury in DRG neurons; J Neurophysiol; 82(5); pp. 2776-2785; Nov. 1999.

Boyden; The chemotactic effect of mixtures of antibody and antigen on polymorphonuclear leucocytes; J Exp Med; 115:453-466; Mar. 1, 1962.

Cao et al.; Template-based synthesis of nanorods, nanowire and nanotube array; Adv Colloid Interface Sci; 136(1-2):45-64; Jan. 15, 2008.

Carter; Potent antibody therapeutics by design; Nat Rev Immunol; 6(5):343-57; May 2006.

Chen et al.; A cell nanoinjector based on carbon nanotubes; Proc Natl Acad Sci U S A.; 104(20):8218-8222; May 15, 2007.

Choi; A Cellular Trojan Horse for Delivery of Therapeutic Nanoparticles into Tumors. Nano Letters; 7(12), pp. 3759-3765; Dec. 2007.

Chu et al.; Electroporation for the efficient transfection of mammalian cells with DNA; Nucleic Acids Res.; 15(3):1311-1326; Feb. 11, 1987.

Das et al.; TiO2 nanotubes on Ti: influence of nanoscale morphology on bone cell-materials interaction; Journal of Biomedical Materials Research Part A; 90(1); pp. 225-237; Jun. 1, 1990.

Daub et al.; Ferromagnetic nanotubes by atomic layer deposition in anodic alumina membranes; J. Appl. Phys.; 101; 09J111 (4 pgs.); May 2007.

Dertinger et al.; Generation of Gradients Having Complex Shapes Using Microfluidic Networks; Anal Chem; 73:1240-1246; Feb. 16, 2001.

Diao et al.; A three-channel microfluidic device for generating static linear gradients and its application to the quantitative analysis of bacterial chemotaxis; Lab Chip; 6(3):381-388; Mar. 2006.

(56) References Cited

OTHER PUBLICATIONS

Dubey et al.; Intercellular nanotubes mediate bacterial communication; Cell; 144(4):590-600; Feb. 2011.
El-Ali et al.; Cells on Chips; Nature; 442(7101):403-411; Jul. 27, 2006.
Engler et al.; Matrix Elasticity Directs Stem Cell Lineage Specification; Cell; 126(4):677-689; Aug. 25, 2006.
Ertan et al.; Electrodeposition of nickel nanowires and nanotubes using various templates; Journal of Experimental Nanoscience; 3 (4); pp. 287-295; Dec. 2008.
Gasiorowski et al.; Alterations in gene expression of human vascular endothelial cells associated with nanotopographic cues; Biomaterials; 31(34):8882-8; Dec. 2010 (author manuscript, 15 pgs.).
Geldof; Nerve-growth-factor-dependent neurite outgrowth assay; a research model for chemotherapy-induced neuropathy; J Cancer Res Clin Oncol; 121(11):657-660; Feb. 1995.
Gheith et al.; Stimulation of Neural Cells by Lateral Currents in Conductive Layer-by-Layer Films of Single-Walled Carbon Nanotubes; Adv Mater; 18(22):2975-2979; Nov. 2006.
Giancotti et al.; Integrin signaling; Science; 285(5430): 1028-1032; Aug. 13, 1999.
Goetz et al.; Computer simulations of bilayer membranes; Self-assembly and interfacial tension; J Chem Phys; 108(7):7397-7409; May 1, 1998.
Griffith et al.; Polymeric biomaterials; Acta Mater; 48(1):263-277; Jan. 1, 2000.
Hanna et al.; Direct cell reprogramming is a stochastic process amenable to acceleration; Nature;462(7273):595-601; Dec. 2009 (auhor manuscript, 17 pgs.).
Haydon et al.; Anaesthesia by the n-alkanes. A comparative study of nerve impulse blockage and the properties of black lipid bilayer membranes; BBA-Biomembranes; 470(1): 17-34; Oct. 3, 1977.
Haydon et al.; The molecular mechanisms of anaesthesia; Nature; 268:356-358; Jul. 28, 1977.
Heath et al.; Nanotechnology and cancer; Annu Rev Med; 59:251-65; Feb. 2008 (author manuscript, 16 pgs.).
James et al.; Patterned protein layers on solid substrates by thin stamp microcontact printing; Langmuir; 14(4); pp. 741-744; Jan. 1998.
Jeon et al.; Generation of Solution and Surface Gradients Using Microfluidic Systems; Langmuir; 16(22):8311-8316; Oct. 31, 2000.
Keenan et al.; Microfluidic fjetsf for generating steady-state gradients of soluble molecules on open surfaces; Appl. Phys. Lett.; 89(11);114103-114103-3; Sep. 11, 2006.
Keenan et al.; Biomoleculargradients in cell culture systems; Lab Chip; 8(1):34-57; Jan. 2008.
Kim et al.; Interfacing Silicon Nanowires with Mammalian Cells; J Am Chem Soc; 129(23):7228-7229; Jun. 13, 2007.
Kinoshita; Electrochemical Uses of Carbon; Electrochem Encycl; p. 11; Jan. 2001.
Knez et al.; Synthesis and Surface Engineering of Complex Nanostructures by Atomic Layer Deposition; Adv Mater; 19(21):3425-3437; Nov. 2007.
Kubota et al.; Role of laminin and basement membrane in the morphological differentiation of human endothelial cells into capillary-like structures; Journal of Cell Biology; 107; pp. 1589-1598; Oct. 1988.
Kumar et al.; The gap junction communication channel; Cell; 84(3):381-8; Feb. 1996.
Kwak et al.; Interfacing inorganic nanowire arrays and living cells for cellular function analysis; Small; 42; pp. 5600-5610; 20 pages; (Author Manuscript) Nov. 2015.
Langer; Drug delivery and targeting; Nature; 392(6679 Suppl):5-10.; Apr. 1998.
Langille et al.; Relationship between blood flow direction and endothelial cell orientation at arterial branch sites in rabbits and mice; Circ Res; 48(4):481-488; Apr. 1981.
Lee et al.; Hydrogels fortissue engineering; Chem Rev; 101(7):1869-1879; Jul. 2001.
Li et al.; Nanotube arrays in porous anodic alumina membranes; J. Mater. Sci. Tech.; 24(4); pp. 550-562; Jul. 2008.
Loh et al.; Nanofountain-probe-based high-resolution patterning and single-cell injection of functionalized nanodiamonds; Small; 5(14):1667-1674; Jul. 2009.
Luo et al.; Synthetic DNA delivery systems; Nat Biotechnol; 18(1):33-7; Jan. 2000.
Lutolf et al.; Synthetic biomaterials as instructive extracellular microenvironments for morphogenesis in tissue engineering; Nat Biotecnol; 23(1):47-55; Jan. 2005.
Malboubi et al.; Effects of the Surface Morphology of Pipette Tip on Giga-seal Formation. Engineering Letters; 17(4), p. 281; Nov. 2009.
Martin; Nanomaterials: a membrane-based synthetic approach; Science; 266 (5193):1961-6.; Dec. 1994.
McKnight et al.; Tracking gene expression after DNA delivery using spatially indexed nanofiber arrays; Nano Letters; 4(7); pp. 1213-1219; May 2004.
Michalet et al.; Quantum dots for live cells, in vivo imaging, and diagnostics; Science; 307(5709):538-44; Jan. 28, 2005 (author manuscript; 16 pgs.).
Oates et al.; Role of titanium surface topography and surface wettability on focal adhesion kinase mediated signaling in fibroblasts; Materials; 4(5); pp. 893-907; May 9, 2011.
Patel, et al.; Spatially controlled cell engineering on biodegradable polymer surfaces; FASEB J; 12(14):1447-1454; Nov. 1998.
Peng et al.; Whole genome expression analysis reveals differential effects of TiO2 nanotubes on vascular cells; Nano Letters; 10(1); pp. 143-148; Jan. 2010.
Persson et al.; Vertical Nanotubes Connected by a Subsurface Nanochannel; 14th Int'l Conference on Miniturized Systems fror Chemistry and Life Sciences; 1862-1864; Oct. 3-7, 2010.
Petronilli et al.; Transient and long-lasting openings of the mitochondrial permeability transition pore can be monitored directly in intact cells by changes in mitochondrial calcein fluorescence; Biophys J.; 76(2):725-34.; Feb. 1999.
Plath et al.; Progress in understanding reprogramming to the induced pluripotent state; Nat Rev Genet.; 12(4):253-265; Apr. 2011 (author manuscript, 26 pgs.).
Qi; Cell adhesion and spreading behavior on vertically aligned silicon nanowire arrays; ACS Appl Mater Interfaces; 1(1):30-4; Jan. 2009.
Ruoslahti; New perspectives in cell adhesion: RGD and integrins; Science; 238(4826):491-7; Oct. 1987.
Safran et al.; Database update: GeneCards version 3: the human gene integrator; Database (Oxford); vol. 2010 (baq020); 16 pgs.; Aug. 2010.
Saito; A Theoretical Study on the Diffusion Current at the Stationary Electrodes of Circular and Narrow Band Types; Rev Polarography; 15(6):177-187; Dec. 1968.
Sakiyama-Elbert et al.; Controlled release of nerve growth factor from a heparin-containing fibrin-based cell ingrowth matrix; J Control Release; 69(1):149-158; Oct. 3, 2000.
Scadden; The stem-cell niche as an entity of action; Nature; 441(7097):1075-1079; Jun. 29, 2006.
Shalek et al.; Vertical silicon nanowires as a universal platform for delivering biomolecules into living cells; Proc Natl Acad Sci U S A.; 107(5):1870-1875; Feb. 2, 2010.
Shamloo et al.; Endothelial cell polarization and chemotaxis in a microfluidic device; Lab Chip; 8(8):1292-1299; Aug. 2008.
Susin et al.; Molecular characterization of mitochondrial apoptosis-inducing factor; Nature; 397; pp. 441-446; Feb. 1999.
Tian et al.; Fabrication of high density metallic nanowires and nanotubes for cell culture studies; Microelectronic Eng; 88(8):1702-1706; Aug. 2011.
Tian et al.; Three-dimensional, flexible nanoscale field-effect transistors as localized bioprobes; Science;329(5993):830-4; Aug. 2010 (author manuscript, 11 pgs.).
Tiscornia et al.; A general method for gene knockdown in mice by using lentiviral vectors expressing small interfering RNA; Proc Natl Acad Sci U S A.; 100(4): 1844-1848; Feb. 18, 2003.
Uhrich et al.; Polymer systems for controlled drug release; Chem Rev; 99 (11):3181-3198; Nov. 10, 1999.

(56) References Cited

OTHER PUBLICATIONS

Vandersarl et al.; Nanostraws for direct fluidic intracellular access; Nano Letters; 12(8); pp. 3881-3886; Dec. 20, 2011.
Verma et al.; Gigaohm resistance membrane seals with stealth probe electrodes; Appl Phys Lett; 97(3):1-3; Jul. 2010.
Verma et al.; Surface-structure-regulated cell-membrane penetration by monolayer-protected nanoparticles; Nat Mater; 7(7):588-595; Jul. 2008 (Author Manuscript; p. 15).
Walker et al.; Effects of flow and diffusion on chemotaxis studies in a microfabricated gradient generator; Lab Chip; 5(6):611-618; Jun. 2005 (Author Manuscript; p. 18).
Wang et al.; Neural stimulation with a carbon nanotube microelectrode array; Nano Lett; 6(9):2043-2048; Sep. 2006.
Wang et al.; Shear stress induces endothelial differentiation from a murine embryonic mesenchymal progenitor cell line; Arterioscler Thromb Vase Biol; 25(9): 1817-1823; Sep. 2005.
Whitesides; The origins and the future of microfluidics; Nature; 442(7101):368-373; Jul. 27, 2006.
Wolfe et al.; U.S. Appl. No. 61/306,778 entitled "Neutral Particle Nanopatterning for Nonplanar Multimodal Neural Probes," filed Feb. 22, 2010.
Wu et al.; Generation of complex, static solution gradients in microfluidic channels; J Am Chem Soc; 128(13):4194-4195; Apr. 5, 2006.
Xiao et al.; Fabrication of Alumina Nanotubes and Nanowires by Etching Porous Alumina Membranes; Nano Lett; 2(11):1293-1297; Oct. 26, 2002.
Xie et al.; Vertical nanopillars for highly localized fluorescence imaging; Proc Natl Acad Sci U S A.; 108(10):3894-9; Mar. 2011.
Xie et al.; Mechanical model of vertical nanowire cell penetration; Nano Letters; 13(12); pp. 6002-6008; Nov. 20, 2013.
Yang et al.; Semiconductor nanowire: What's Next?; Nano Letters; 10; pp. 1529-1536; May 2010.
Yu et al.; Diffusion dependent cell behavior in microenvironments; Lab Chip; 5(10): 1089-1095; Oct. 2005.
Yu et al.; Nano Wheat Fields Prepared by Plasma-Etching Gold Nanowire-Containing Membranes; Nano Lett; 3(6);815-818; Mar. 20, 2003.
Zeck et al.; Noninvasive neuroelectronic interfacing with synaptically connected snail neurons immobilized on a semiconductor chip; Proc Natl Acad Sci U S A.; 98(18):10457-62; Aug. 2001.
Zicha et al.; A new direct-viewing chemotaxis chamber; J Cell Sci; 99(4);769-775; Aug. 1991.
Zigmond; Orientation chamber in chemotaxis; Methods Enzymol; 162:65-72; Oct. 12, 1988.
Hjort et al.; U.S. Appl. No. 16/038,062 entitled "Apparatuses and methods using nanostraws to deliver biologically relevant cargo into non-adherent cells," filed Jul. 17, 2018.
Cao et al.; Non destructive nanostraw intracellular sampling for longitudinal call monitoring; Proceedings of the National Academy of Sciences; 114(10); pp. E1866-E1874; XP002797487; Mar. 1, 2017.
Liu et al.; Voyage inside the cell: Microsystems and nanoengineering for intracellular measurement and manipulation, Microsystems & Nanoengineering; 1(1); XP055666437; DOI: 10.1038/micronano.2015.20; Sep. 14, 2015.
Chang et al.; Dielectrophoresis-assisted 3D nanoelectroporation for non-viral cell transfection in adoptive immunotherapy. Lab on a Chip. 15(15); pp. 3147-3153; Jun. 2015.
Chang et al.; Magnetic tweezers-based 3D microchannel electroporation for high-throughput gene transfection in living cells; Small; 11(15); pp. 1818-1828; 20 pages (Author Manuscript); Apr. 2015.
Wu et al.; Efficient expression of foreign genes in human CD34+ hematopoietic precursor cells using electroporation; Gene Therapy; 8(5);, pp. 384-390; Mar. 2001.

\* cited by examiner

| Experimental Parameters | |
|---|---|
| Number of Cells | 25,000 to 50,000 cells per Nanostraw Well |
| Media Volume inside Nanostraw Well | 325 to 375 microliters for cell culture |
| Volume Solution below Nanostraw Well | 65 to 75 microliters molecular cargo in solution |
| Quantity of Molecular Cargo | 5 to 10 microgram pmCherry (per 50,000 cells) |
| Condition Compatibility | UV, 70% ethanol in water, Incubator, light microscope |
| Cell Types | Cell line, Primary cells, Stem cells |
| Tube Material Biocompatibility | Polycarbonate |
| Tape Material Biocompatibility | Acrylic Adhesive |

FIG. 3A

| Technical Parameters | |
|---|---|
| Top Electrode Material | Aluminum, Pt |
| Bottom Electrode Material | Aluminum, Pt |
| Top Electrode Shape | Disk (.15cm to .2cm) |
| Bottom Electrode Shape | Planar (cover entire bottom) |
| Top Electrode Distance from Membrane | .5 cm to .75 cm |
| Pulse Voltage | 10 to 50V (depending cell type) |
| Pulse Width | 100 to 200 microseconds |
| Pulse Frequency | 20 to 40 Hz |
| Net time with Pulse | 40 to 60 seconds |

FIG. 3B

| | TEMPERATURE (CELSIUS) | | | GAS PARAMETERS | | | | | |
|---|---|---|---|---|---|---|---|---|---|
| PRECURSOR | INLET | CHAMBER | OULET | EXHAUST | FLOW RATE (sccm) | PRESS. (mTorr) | PULSE (S) | EXPOSURE (S) | PUMP (S) | CYCLES (#) |
| E | 100 | 100 | 120 | 150 | 10 | 5.00E-01 | 0.025 | 5 | 20 | 80 |
| 60 | | | | | | | | | | |

FIG. 7
(CONT.)

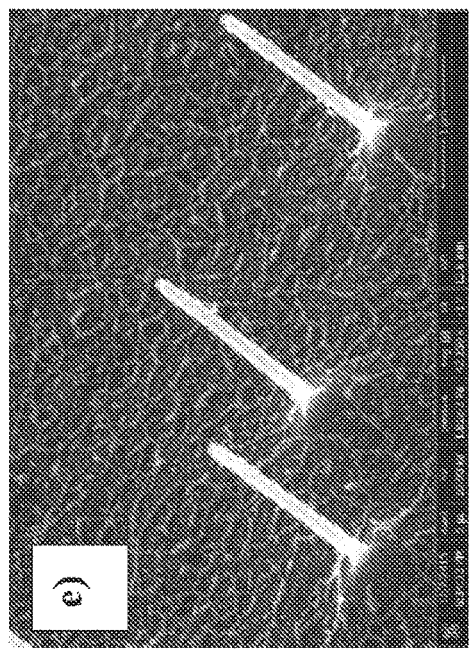
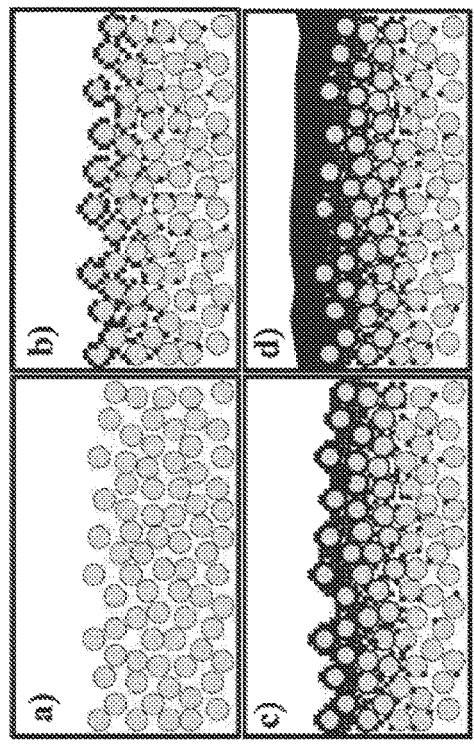
FIG. 8
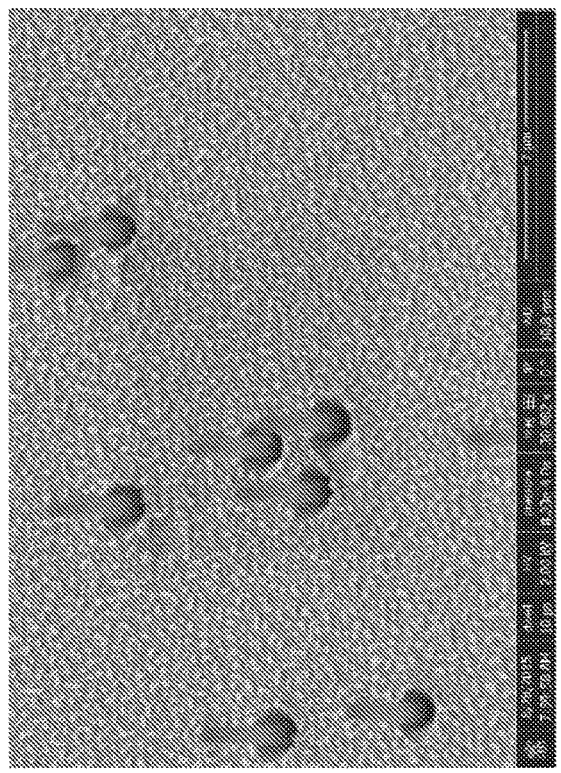
FIG. 9

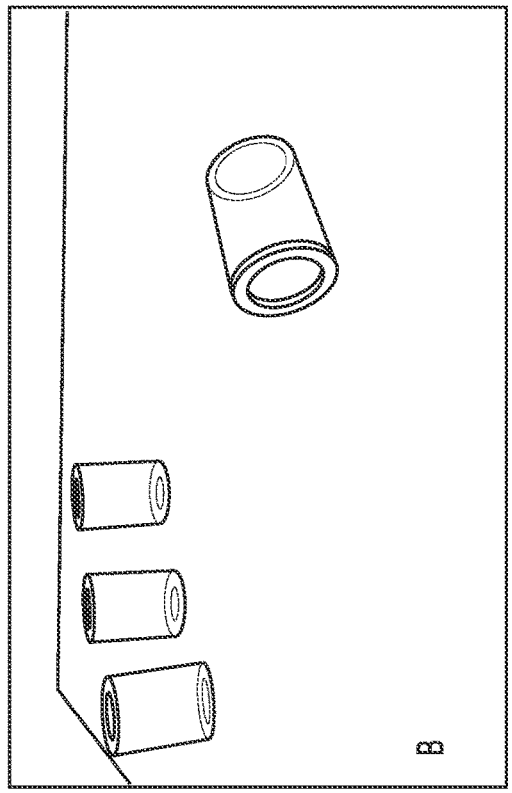
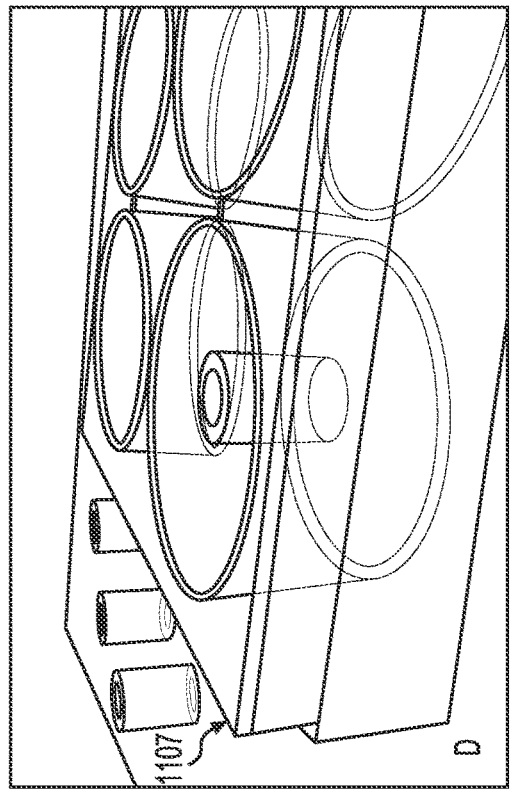
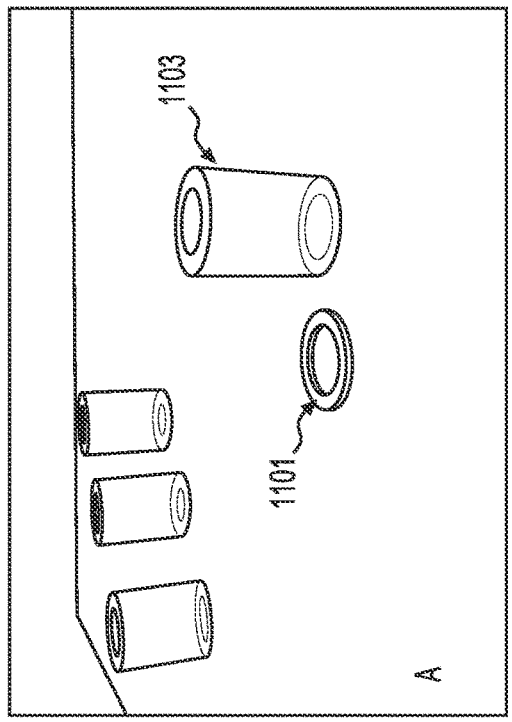
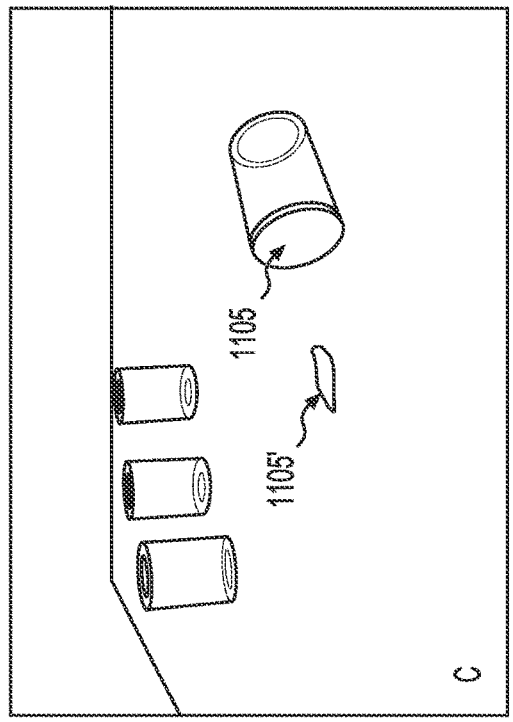
FIG. 11

NANOSTRAW WELL INSERT DEVICES FOR IMPROVED CELL TRANSFECTION AND VIABILITY

CROSS REFERENCE TO RELATED APPLICATIONS

This patent application claims priority to U.S. provisional patent application No. 62/347,928, filed Jun. 9, 2016, which is herein incorporated by reference in its entirety.

STATEMENT AS TO FEDERALLY SPONSORED RESEARCH

This invention was made with Government support under contract 1549696 awarded by the National Science Foundation. The Government has certain rights in the invention.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND

Transfection, or generally the delivery of molecular species across the lipid bilayer and into the cytosol or nucleus, is a powerful analytical tool with many applications spanning cell reprogramming, intracellular imaging and sensing, molecular farming, siRNA knockouts, drug screening, and pharmaceutical therapies. To meet such a wide spectrum of application, biologists have developed conventional transfection approaches which broadly fall into biological, chemical, and physical classes, with physically mediated techniques dominating emerging technologies. These methods all revolve around traversing the membrane with as little detriment to the cell and as high efficiency as possible. However, despite almost half a century of technique innovation, development, and optimization, the transfection field lacks a universal tool for delivery into the cell; this is to say, existing methods all have advantages and disadvantages which depend highly on experimental designs and objectives. In principle, the ideal transfection technique would permit the efficient transport of cargo, irrespective of size or structure, into any cell type with high throughput and preservation of cell physiology.

VanDersarl et. al. (U.S. Pat. No. 9,266,725) described a simple, yet elegant biomimetic innovation in the bionanotechnology field in 2012 involving the processing of commonly used nanoporous membrane filters into nanofluidic substrates containing cell-penetrating architectures, or Nanostraws. Nanostraws are essentially metal oxide nanotube structures, with diameter on the order a 100 nm, embedded in polymer films. Nanostraw technology uniquely establishes non-destructive intracellular access in real-time, vital for the delivery, or extraction, of bioactive molecular cargo. Cells cultured on Nanostraw devices are spontaneously penetrated, providing a stable, external handle on the delivery of fluidic material species into, or out of cells. Moreover, enhanced penetration in combination with electroporation has been suggested, which can in turn result in much higher delivery rates.

The work herein is motivated, from a much broader perspective, with the goal of translating Nanostraw technology from primary users, i.e., researchers in an academic nanoscience lab, to secondary users such as adjacent academic biology labs that may accelerate both the development and real impact of the technology. The barrier to this sort of technology transfer in the field of nanobiotechnology is typically steep, as it requires expertise and collaboration in both nanotech and biotech. To this end, the methods and apparatuses described herein may provide repeatable and uniform device performances, measured in terms of transfection efficiency and cell viability. Further, the method and apparatuses described herein may provide nanostraw device fabrication and to optimized performance across multiple cell types.

SUMMARY OF THE DISCLOSURE

Described herein are nanostraw well insert apparatuses (e.g., devices and systems) that include nanotubes extending through and out of a membrane so that a material can pass through the membrane from a fluid reservoir depot and into a cell grown onto the nanotubes when electrical energy (e.g., electroporation energy) is applied. In particular, the apparatuses (device and systems) and methods described herein may be adapted for long term cell growth viability (>5 days) and transfection efficiency (e.g., >70%). These apparatuses may be readily integratable into cell culturing processes for improved transfection efficiency, intracellular transport, and cell viability.

For example, described herein are nanostraw cell culture systems including one or more nanostraw well insert devices and/or one or more adapters configured to hold the nanostraw well insert device(s). A nanostraw cell culture system for long-term cell growth and transfection may include: a nanostraw well insert device and an adapter configured to hold the nanostraw well insert device. Any appropriate nanostraw well insert devices may be used, including those that typically include a cylindrical wall, a membrane from which a plurality of nanostraws project; and a biocompatible adhesive connecting the membrane across a base of the cylindrical wall to form a well, wherein the nanostraws project into the well greater than 0.1 microns (e.g., between 0.1 and 25 microns, between 0.5 and 5 microns, between 1 and 3 microns, etc.). As will be described in greater detail herein, in some variations it is particularly advantageous to use nanostraws formed of hafnia. The adapter that is configured to hold the nanostraw well insert device may include: a base comprising a base electrode, wherein the based is configured to securely hold the cylindrical wall of the nanostraw well insert device so that the plurality of nanostraws are in fluid communication with a reservoir depot over the base electrode; a cover comprising a top electrode, wherein the cover is configured to engage the base so that when a nanostraw well insert device is held within the base, the top electrode is separated from the base electrode by a distance, e.g., of between 0.25 cm and 1.25 cm with the nanostraw insert device enclosed there between; a first electrical contact on an outer surface of the adapter, wherein the first electrical contact is in electrical communication with the base electrode; and a second electrical contact on the outer surface of the adapter, wherein the second electrical contact is in electrical communication with the top electrode.

Any of the nanostraw well insert devices may have a cylindrical wall. The cylinder may have any appropriate height (e.g., between 1 cm and 5 cm, between 1 cm and 3 cm, between 1 cm and 2 cm, etc.) and width (e.g., an outer diameter, OD, between about 0.5 cm and 5 cm, between 0.5 cm and 2 cm, between 0.75 cm and 1.5 cm, etc. and an inner diameter, ID, of between 0.3 cm and 5 cm, e.g., between 0.3 cm and 2 cm, between 0.4 cm and 1.4 cm, etc.). The transverse cross-section of the cylinder may be round, oval, triangular, rectangular, square, pentagonal, octagonal, etc.

The membrane may be a porous membrane wherein the plurality of nanostraws project greater than 0.1 microns (e.g., between 0.1 and 25 microns, between 0.5 and 5 microns, etc.) above the membrane on the inside of the well formed by the cylindrical wall. The pore diameter of the plurality of nanostraws may be between 10 nm and 1000 nm (e.g., between 10 nm and 900 nm, between 30 nm and 800 nm, between 70 nm and 400 nm, between 80 nm and 200 nm; between 80 nm and 150 nm, etc.). The biocompatible adhesive may typically be an acrylic adhesive. In particular, the biocompatible adhesive may be a double-sided tape, such as an acrylic double-sided tape.

An adapter configured to hold the nanostraw well insert device may generally be configured to secure the one or more nanostraw well insert devices within the adapter, so that the bottom side of the membrane (e.g., the bottom openings of the nanostraws) is in fluid communication with a reservoir depot that is itself in electrical communication with the base electrode. The inside surface of the adapter may be configured to mate with and secure the cylindrical wall and/or bottom rim of the nanostraw well insert device within a cavity so that the nanostraw well insert device is supported against the reservoir depot. The reservoir depot may be formed at least in part by the base electrode at the bottom of the cavity. The adapter may generally be adapted to vent air from between the reservoir depot a bottom of the nanostraw well insert, e.g., to prevent entrapment of air (e.g., bubbles) between the bottom of the membrane and the reservoir depot.

The cover of the adapter typically fits over the nanostraw well insert device and mates with the base, so as to enclose the nanostraw well insert device within the adapter. The cover of the adapter may be generally configured to secure over the base so that the nanostraw well insert device is completely enclosed therein.

The cover also holds the top electrode and is configured to position the top electrode a predetermined spacing distance from the base electrode with the nanostraw well insert device between, so that any cells growing over the nanostraw of the membrane of the device are positioned between the top and base electrodes. The cover may secure to the base with a friction fit, a snap fit, a screw-fit, etc. Electrical contacts on the outside of the adapter may be connected to voltage source to apply energy to controllably (and with high efficiency) transfer a material in the fluid from the reservoir depot through the nanotubes and into the one or more cells without damaging the cells.

For example, the first electrical contact may be on a top of the cover and the second electrical contact may be on a bottom of the base. When the cover is engaged with the base, the top electrode may be separated from the base electrode by between, e.g., 0.3 cm and 0.8 cm.

The top electrode may have a surface area that is smaller than the surface area of the base electrode. Both electrodes may be any conductive material (the same or different), including platinum and/or aluminum. For example, the top electrode may be a disk electrode (or a disk surface) having a diameter of between 0.1 and 0.4 cm (e.g., 0.1 and 0.3 cm, 0.1 and 0.25 cm, 0.12 and 0.22 cm, 0.15 and 0.2 cm, etc.); the base may be a planar electrode that covers much (>80%, >90%, 100%) of the bottom of the nanostraw well insert device bottom membrane. The reservoir depot may be formed at least in part by one or more sides of the base electrode. For example, the base electrode may include a concave surface forming all or a portion of the reservoir depot, into which a material (e.g., fluid including the material to be transfected into the one or more cells) is placed to be in contact with the bottom of the nanostraw well insert device.

As mentioned, also described herein are nanostraw well insert devices for long-term cell growth and transfection. Either the nanostraw well insert device of the adapter may be used independently or as part of a system. For example, a nanostraw well insert device may include: a cylindrical wall; a membrane through which a plurality of hafnia (HfO2) nanostraws project; and a biocompatible adhesive connecting the membrane across a base of the cylindrical wall to form a well, wherein the nanostraws project into the well for greater than 0.1 microns (e.g., between 0.5 and 5 microns, etc.).

The cylindrical wall may be any appropriate material, including in particular a polycarbonate tube. As mentioned, the nanostraw well insert device may also include an adhesive between the membrane and the cylindrical wall (tube); for example, an acrylic adhesive may be used between the cylindrical wall and the membrane, such a double-sided acrylic tape.

The plurality of hafnia nanostraws have a pore size of between 10 nm and 1000 nm (e.g., between 10 nm and 900 nm, between 30 and 500 nm, e.g., between 70 nm and 130 nm, between 80 nm and 120 nm, etc.). The plurality of hafnia nanostraws project into the well greater than 0.1 microns (e.g., between 0.1 and 25 microns, between 0.1 and 5 microns, between 0.5 and 3 microns, etc.). Typically, the plurality of nanostraws each comprise a continuous channel extending from outside of the device, through the membrane and into the well.

Although the apparatuses and methods described herein typically refer to nanostraws, the method and apparatuses described herein may also be used with nanowires.

Also described herein are method of using any of the apparatuses described herein to grow and/or transfect cells. For example, described herein are methods of culturing and transfecting cells comprising: culturing one or more cells in a nanostraw well insert device for longer than five days, wherein the nanostraw well insert device comprises a cylindrical wall and a membrane extending across a base of the cylindrical wall to form a well, wherein a plurality of nanostraws project through the membrane and into the well greater than 0.1 microns (e.g., between 0.5 and 5 microns, etc.); placing the nanostraw well insert device into a base of an adapter so that the plurality of nanostraws are in fluid communication with a reservoir depot in the base, wherein the reservoir depot is in electrical communication with a base electrode in the base; placing a cover over the base, wherein the cover comprises a top electrode, so that the top electrode extends into the nanostraw well insert device and the top electrode is separated from the base electrode by between 0.25 and 1.25 cm; applying a voltage between the base electrode and the top electrode to deliver a material from the reservoir depot, through the plurality of nanostraws and into the one or more cells; and removing the nanostraw well insert from the adapter and culturing the one or more cells in the nanostraw well insert.

Applying the voltage may comprise applying the voltage between a first electrical contact on an outside surface of the adapter and a second electrical contact on an outside of surface of the adapter, wherein the first electrical contact is in electrical communication with the top electrode inside the adapter and the second electrical contact is in electrical communication with the base electrode inside the adapter. The voltage may be between about 0.1 V and 20 V, including in particular, 15V or less.

Any of these methods may include imaging the one or more cells in the nanostraw well insert device either before or after applying voltage to deliver the target materials into the cells. Applying the voltage may comprise applying a pulse width of between, e.g., 10 and 500 microseconds (e.g., 50 and 400 microseconds, 70 and 300 microseconds, 100 to 200 microseconds, etc.), at a pulse frequency of between, e.g., 1 Hz and 10 kHz (e.g., between 15 Hz to 800 Hz, 20 Hz to 400 Hz, between 10 Hz and 250 Hz, etc.). The total duration of stimulation may be between 1 and 600 seconds (e.g., the net time with a pulse may be between 20 seconds and 120 seconds, between 25 seconds and 100 seconds, between 30 seconds and 80 seconds, between 40 seconds and 60 seconds, etc.).

Culturing the cell may comprise culturing the cells on a plurality of hafnia (HfO2) nanostraws. In general, culturing may include culturing with the nanostraw well insert device in a multi-well dish (e.g., a 2, 4, 6, 8, 16, 32, etc. multi-well dish); growth media may generally be placed both in the nanostraw well insert device (e.g., within the well) and may also be placed around the nanostraw well insert devices within the multi-well dish. The cover of the multi-well dish may be placed over the nanostraw well insert device(s).

In any of these methods, the method may also include loading the material into the reservoir depot prior to placing the nanostraw well insert device into the base.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 2A illustrates a general nanostraw well insert device during transfection. In this example, the device consists of a polycarbonate tube with a nanostraw membrane attached to the bottom so as to make a culture well. Cells are cultured directly in the device well with media within the well. For transfection via electroporation, the device is placed into contact with the cargo reservoir beneath the membrane, containing the molecular species to be delivered (shown here as small spheres in solution; e.g., DNA/RNA in water). Electric pulses are fired across two platinum electrodes to open pores in the cell membrane, enabling intracellular access. (In FIG. 2A, the cells and nanostraws are not drawn to scale).

FIG. 3A is a table illustrating exemplary parameters for the nanostraw well insert devices shown in FIGS. 2A-2D. FIG. 3B illustrates exemplary technical parameters for the nanostraw well insert device shown in FIGS. 2A-2D. Note that the values provided in the tables of FIGS. 3A and 3B represent just one example, as described more fully herein, other examples may be used.

FIGS. 4A-4C illustrates a process flow schematic for formation of a nanostraw well insertion device. In FIG. 4A, PCTE membranes are mounted on a p-type (100) silicon carrier wafer. FIG. 4 C.1 to C.3 illustrate the assembly of nanostraw well insert devices ready for biological testing in culture plate.

In FIG. 6A the $Al_2O_3$ film process is initiated by addition of the aluminum carrying precursor (TMA, or trimethly aluminum). In FIG. 613, TMA precursor reacts with a naturally adsorbed surface hydroxyl group on the substrate to bind aluminum to oxygen and release methane as a byproduct. In FIG. 6C, after all, or mostly all, surface oxygen sites have been reacted with TMA precursor molecules, $H_2O$ vapor is pumped into the chamber. In FIG. 6D, water molecules react with the surface alumina atoms to form a "monolayer" of alumina, $Al_2O_3$. This process is repeated until the desired film thickness is achieved.

FIGS. 8A-8D illustrates one possible mechanism for atomic layer deposition of oxide material onto polymer substrate with increasing number of cycles. In FIG. 8A, diffusion of gaseous precursor is blocked after a critical cycle number and uneven diffusion is expressed as surface roughness. The thickness of alumina deposition on silicon as measured via ellipsometry is comparable to thicknesses estimated from SEM, as seen in FIG. 8E. Thickness observations from SEM may be skewed from a few possible artifact sources: amorphous material from polymer outgassing may deposit during the ALD vacuum conditions, silver/gold sputtering for SEM preparation adds thickness, and significant surface charging during imaging. However, open-pores can readily be imaged via SEM and aid in quality control.

FIG. 9 is an SEM showing silica nanostraws (100 nm pore size). While cell viability on silica architectures was quite excellent, standard biological protocols for transfection were less efficient than comparable alumina straws.

In FIG. 10A, hafnia nanostraws were successfully fabricated using a Savannah 200 (Cambridge Nanotech). FIGS. 10B and 10C show SEM images at different magnifications of hafnia nanostraws, showing clean, open pores that appear to have uniform diameters along the entirety of the straw length.

FIGS. 11A-11D illustrate one method of assembling at least a portion of a nanostraw well insert apparatus as described herein. FIG. 11A shows a tubular body (e.g. a polycarbonate tube) and an adhesive (shown as double-stick tape); FIG. 11B shows the tubular body with the adhesive on the bottom surface; in FIG. 11C, the nanostraws on the substrate are attached via the double-sided tape to the tubular body. The insert is shown inserted into a well in FIG. 11D.

DETAILED DESCRIPTION

Transfection, or the transport and integration of external material, typically nucleic acids, into the cytosol and/or nucleus of a living cell, is an essential technique for a wide set of modern biological, biomedical, and biotechnological methods, including cell reprogramming, intracellular imaging and sensing, molecular farming, siRNA knockouts, drug screening, and pharmaceutical therapies.

VanDersarl et. al. have previously reported a simple biomimetic nanostructure, or "nanostraw," that establishes continuous fluidic access into the cell interior for the purpose of intracellular delivery, and extraction, of molecular cargo. Nanostraws are metal oxide nanotube structures, with diameter on the order of 100 nm, embedded in widely used polymer membrane filters. Cells cultured on nanostraw devices are spontaneously penetrated, providing a stable, external handle on the delivery of fluidic material species into cells. Nanostraws have been demonstrated to successfully transmit molecules from ions to 6000 base pair DNA structures over relatively short time scales. Moreover, existing literature highlights the compounded effects of integrated electroporation with nanostraw access for delivery of cargos of interest. The stability, versatility, and non-invasive nature of the Nanostraw platform position the technology as a likely candidate for a universal solution for intracellular access with the purpose of understanding the underlying biology of the cell.

Figure 4:
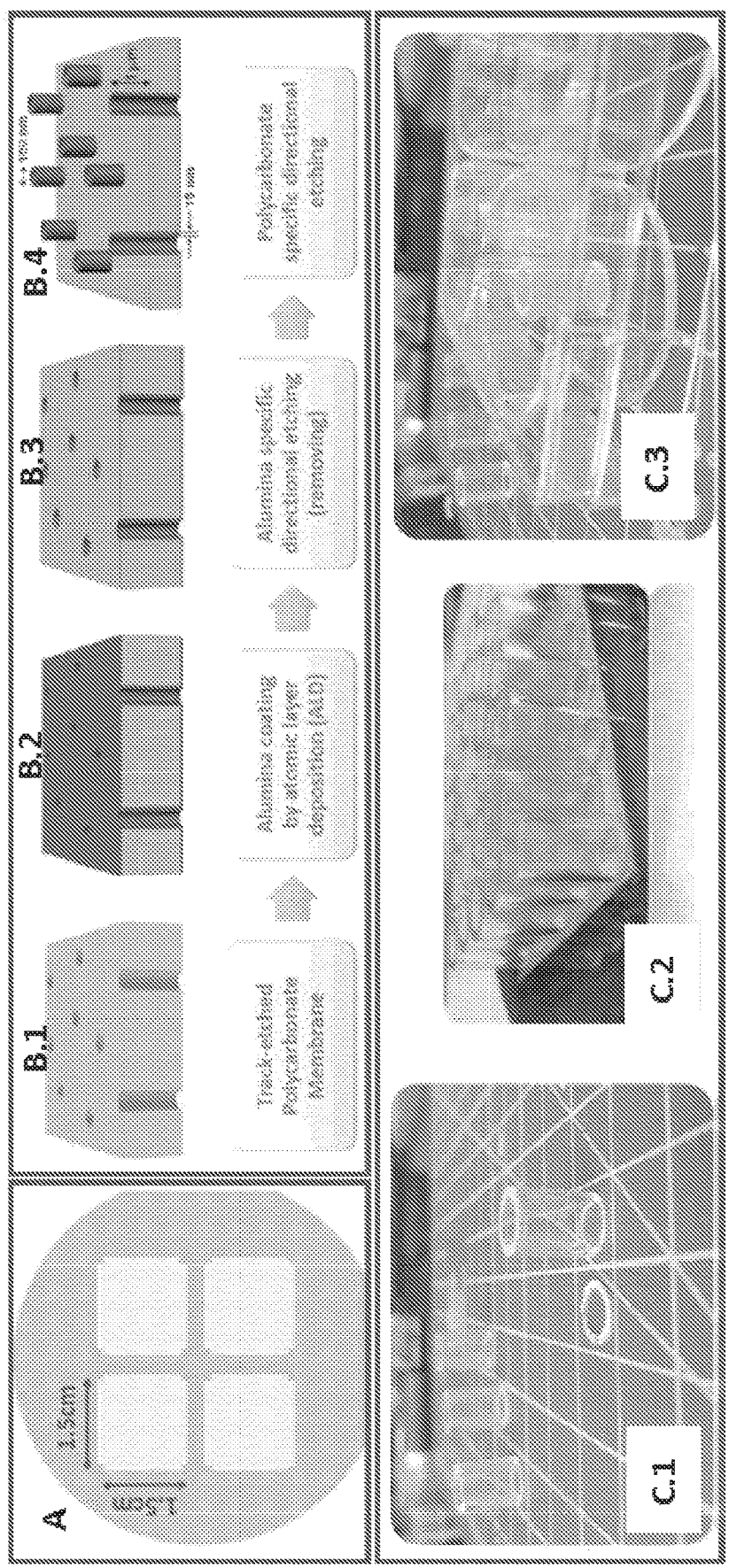
FIGS. 4 B.1 to B.4 illustrate fabrication of a membrane including nanostraws.

FIG. 4, B1-B4 illustrates an overview of nanostraw membrane fabrication, showing a three step process. Track-etched membrane filters (B.1) are coated via metal oxide atomic layer deposition (B.2). Following the deposition process, the top metal oxide surface layer is reactive ion etched in plasma (B.3). Nanostraw length is controlled via oxygen plasma etching (B.4), selective to the supportive polymer matrix. Provided the starting track-etched membrane pore sizes are selected, all Nanostraw dimensions can be tailored: straw length, density, outer and inner diameter.

Despite consistent confirmation of delivery/extraction of materials across the cell-membrane for model cells (e.g., CHO, HEK293), straw-cytosol spontaneous penetration events have been recently reported as occurring stochastically with a probability of less than 10% (~5 to 15 penetrations/cell). While continuous, leaky access may be undesirable and detrimental to the cell, increased penetration requires an induced field which can certainly complicate design and optimization. In particular, electroporation has demonstrated to increase penetration and delivery events; however, internal observations have reported relatively non-uniform spatial transfection efficiencies (TE) with respect to centimeter-squared device areas (~100,000 cells/monolayer). Relatively improbable spontaneous penetration and spatially non-uniform transfection efficiencies with respect to an induced field have proven to be problematic for existing device fabrication.

Described herein are nanostraw apparatuses and methods that may address many of these issues. For example, the methods and apparatuses described herein may be used with a wide variety of biological applications, such as immune cell reprogramming and stem cell modification. The nanostraw tools described herein may have enhanced uniformity and, in particular, may provide increased cell viability compared to prior devices.

The production of nanostraw well inserts for intercellular delivery is a five step process: (1) mounting and positioning of track-etched polymer membrane filters on silicon carrier wafers (FIG. 4A); (2) conformal atomic layer deposition (ALD) of metal oxide onto track-etched nanoporous polymer membrane (FIGS. 4 B.1 and B.2); directional ion etching of the top surface of ALD to expose polymer (FIG. 4 B.3); oxygen plasma etching of polymer membrane to control nanostraw length (e.g., 1 to 3 microns) (FIG. 4 B.4); and assembly of nanostraw well insert devices via adhesive annular tape and trimming of excess nanostraw membrane (FIG. 4, C.1 to C.3).

Figure 5:
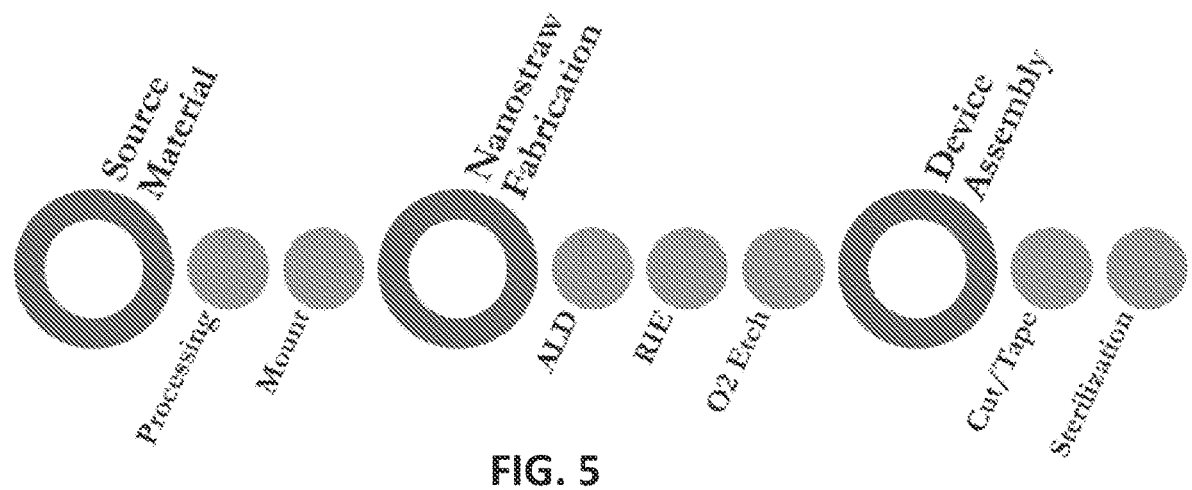
FIG. 5 is a graph showing an overview of the production of a nanostraw insert.
Figure 6:
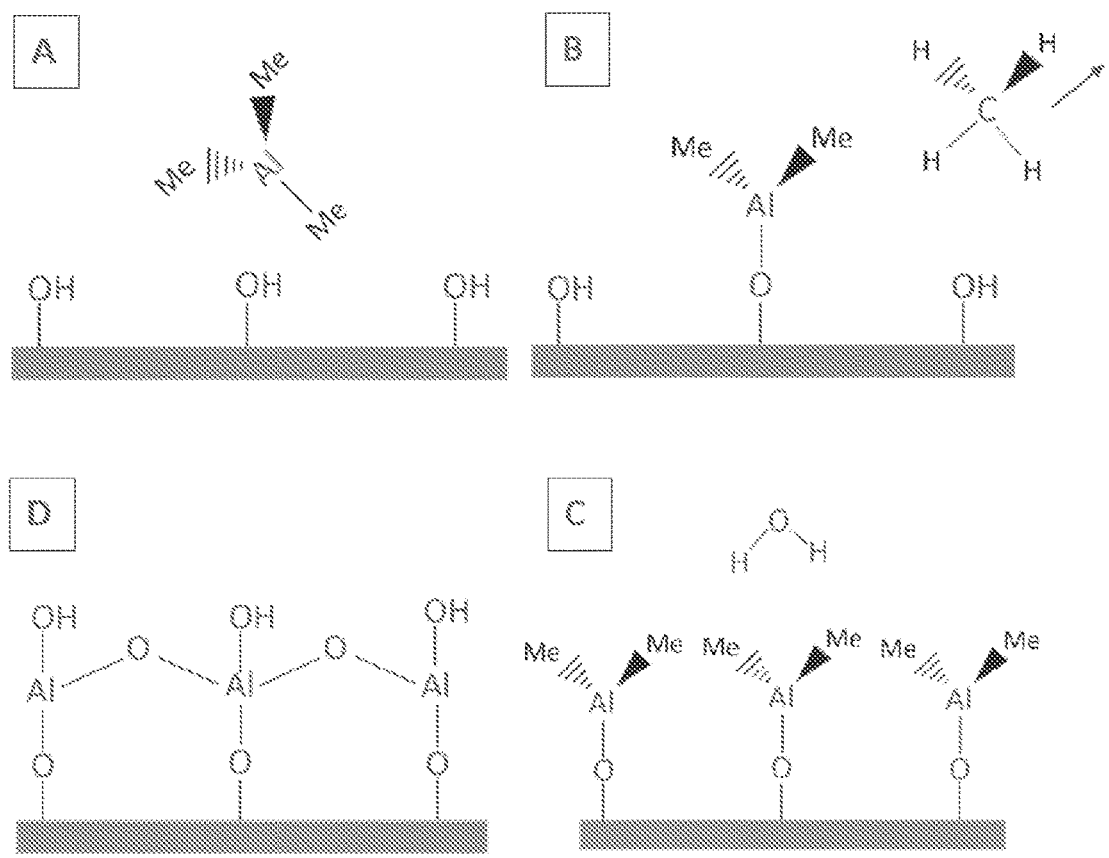
FIGS. 6A-6D illustrate atomic layer deposition of an alumina layer on a substrate. The process generally includes alternating pulses of reactive gaseous precursors to generate layer-by-layer film growth.

As illustrated in FIG. 5, the production of a nanostraw insert can be broken down into three production nodes based on considerations with respect to fixed dimensions, flexible dimensions, and form factor. Commercially available polymer membranes provide a range of fixed starting dimensions such as nanostraw density (e.g., $10^6$ pores/cm$^2$ to $10^9$ pores/cm$^2$), outer straw diameters (e.g., 50 nm to 10 µm), and membrane thicknesses (e.g., 5 µm to 20 µm). Flexible dimensions/properties such as wall thickness, inner diameter, straw height, roughness, tip sharpness, and biological compatibility (functionalization) are governed by the material choice for ALD as well as the respective deposition and etching processing parameters. See, e.g., FIGS. 2A-2D. While a variety of microfluidic designs may be employed, the nanostraw well insert apparatuses described herein may be configured as described herein.

FIG. 5 is a process flow showing nodes of a nanostraw well insert production. Starting with the source material (step I) preparation, then nanostraw fabrication (steps II, III, and IV), and concluding with device assembly (step V). The first node (i.e. source material) may include choice and preparation of polymer material and/or density. Processing steps at the second node (i.e. nanostraw fabrication) can be tailored to meet nanostraw dimensions such as inner diameter, length and straw material. The third node (device assembly) may set the device form factor.

Compared to prior methods, the methods described herein may yield both uniform nanostraw well devices and transfection efficiencies consistently over 75 percent with standard cell lines.

A track etched polymer may be chosen depending on relative availability and industrial experience. Ultimately, the polymer material must be compatible with cell culturing, deposition, and plasma process conditions, as discussed below. Polycarbonate (PC) track etched (PCTE) membranes have been used for large scale filtration and cell culture applications. Hence, PCTE is one example of a nanoporous membrane substrate for nanostraw fabrication described herein. In addition to PCTE also described herein are substrates of PET, or polyethylene terephthalate, which the inventors have identified as suitable for fabrication, culturing, and imaging conditions due to its amenable glass transition temperature and high degree of transparency.

In one example, the roll-to-roll manufacturing of PC films is an exemplary process that may be used. The process consists of extruding PC films to a prescribed thickness (~5-20 μm), exposing the film to beta particle penetration of a particular density (2-4×10$^7$ pores/cm2 for nanostraw fabrication). Once pores have been introduced, process engineers wet etch the pores in a combination of UV light and basic solution (1M NaOH) to a desired diameter (<100 nm), and modifying with selected wetting agents to tune hydrophobicity. An example of a typically used wetting agent is polyvinylpyrrolidone (PVP) which is used to increase surface hydrophilicity for cell culture.

Upon retrieval of processed PCTE and prior to additional processing steps, membranes are cut into 1.5 cm×1.5 cm square pieces using surgical scissors, positioned in quadrants on p-type (100) silicon wafers and mounted at the corners via kapton processing tape. The square length is determined by the size of the nanostraw well device such that four devices can be produced per membrane square, i.e. 16 devices/wafer. Despite sacrificing some interstitial membrane material to device fabrication, membranes are positioned as such for logging within-batch processing conditions to further develop quality assurance protocols. Moreover, the leftover interstitial membrane material is often used for destructive characterization such as SEM. Silver sputtering has been observed to change the Nanostraw surface chemistry which effectively renders nanostraws cytotoxic. However, in the direction of developing quality control procedures, gold sputtering may potentially be used examine the link between straw morphology and transfection performance as Au has been demonstrated to be more biocompatible.

Atomic layer deposition (ALD) is a chemical vapor deposition technique that can be enhanced thermally and/or by the utilization of plasma (PEALD) or radical species. The atomic layer epitaxy, or ALE, technique was modified in the late 1990's to include non-epitaxial deposition and has been recently referred to as atomic layer deposition. ALD is commonly used in a variety of thin film technologies, including but not limited to metal oxide high-k gate materials for MOSFET technologies and abrasive/protective coatings for polymers. The development and enabling of ALD over the recent years can be characterized by advancements in scalable processing techniques and a widening range of processing materials and precursors, both of which have expanded the market for ALD applications in terms of cost-effectiveness and material compatibility.

The fundamental principle for ALD is the layer-by-layer growth of films on a heated substrate. In this deposition method, two chemical precursors are selected for their high relative reactivity and introduced to the process chambers sequentially so as to control reaction at the surface. In principle, each reaction step is self-terminating. The first step involves exposing the substrate surface to the first reactant precursor and then pumping the reactant away. During this exposure the first reactant effectively leaves behind a "monolayer" of molecules adsorbed to the substrate surface. The chamber is then evacuated and a second reactant is introduced into the chamber. This second precursor reacts with the monolayer of the first reactant, forming one layer (typically less than a full layer) of the solid film being sought. After this, the remaining second reactant and any gas phase reaction products are removed from the chamber. This process, diagrammatically illustrated in FIG. 6A-6D, is repeated as many times as necessary to grow a film of the desired thickness.

While atomic layer deposition is traditionally marked by rather slow deposition rates (on the order of an angstrom/min) relative to other chemical vapor deposition techniques, the advantages of ALD include: "digital" thickness control on the atomic level (e.g., film thickness can be atomically controlled by varying the number of ALD cycles); relatively low temperatures and pressures, which enables compatibility with less robust substrates, such as polymers and some papers; conformal film growth over high aspect ratios on topographical substrates (gas precursors can reach any exposed surface, i.e. coverage is not limited by line-of-sight vapor source, in the case of non-PEALD processes); and relatively cheap deposition with an economy of scale. Ultrafast deposition (~0.5 nm/sec, on the order of 300× the rate of traditional ALD) is may be achieved with roll-to-roll coating and parallel spatial processing.

The nanostraw production described herein may exploit this conformal film deposition, along with selective etchings, to leverage nanometer resolution for growth of high-aspect ratio structures.

The parameters for controlling the ALD process may include temperature set points throughout the system, precursor (TMA and $H_2O$ for $Al_2O_3$) flow characteristics, and delay time for system equilibration. Film uniformity may be enhanced with oxygen plasma cleaning of the membranes prior to initiating the ALD process. The standard film growth parameter used yields an approximate deposition of 10 nm+/−1 nm with a wafer uniformity within 5% on p-type silicon (see, e.g. 5 point analysis in FIG. 7D). $Al_2O_3$ film thicknesses on silicon were measured via ellipsometry with three angstrom resolution. Alumina deposition thickness on silicon was used to correlate to deposition thickness on polycarbonate. Actual ALD thickness was measured as the side wall thickness of fully fabricated nanostraws using an FEI scanning electron microscope (see, e.g., FIG. 8E, normal to electron beam).

Figure 7:
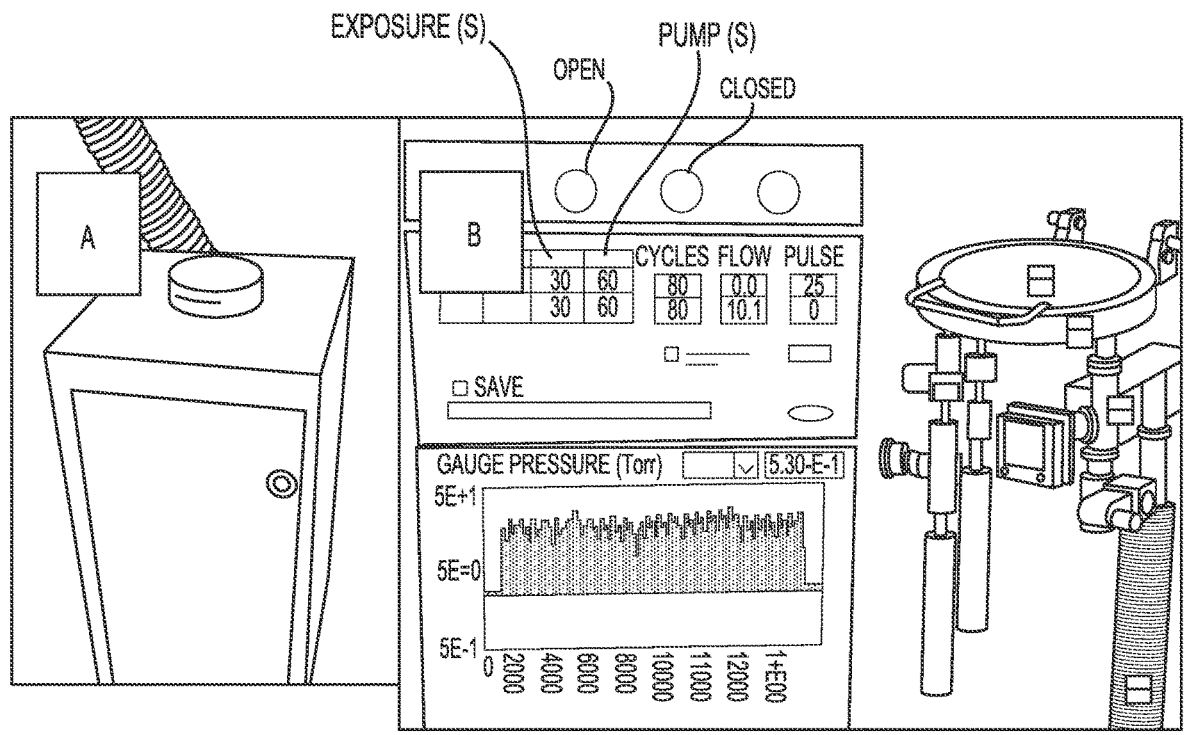
FIG. 7A shows a Savannah 100 apparatus (Cambridge NanoTech) that may be used to grow an $Al_2O_3$ film.
FIG. 7B shows a user interface for operating the device shown in FIG. 7A.
In FIG. 7C, the pressure profiles are used to monitor precursor pulse and chamber purge characteristics for quality control purposes.
FIGS. 7D and 7E show five-point ellipsometry thickness uniformity test reports, showing 10 nm+/−1 nm thick alumina films on silicon via a standard ALD deposition protocol.

In FIG. 7, a standard $Al_2O_3$ film was grown using a Savannah 100 apparatus (Cambridge NanoTech), shown in FIG. 7A. FIG. 7B, shows a user interface for operating the device shown in FIG. 7A. In FIG. 7C, the pressure profiles are used to monitor precursor pulse and chamber purge characteristics for quality control purposes. FIGS. 7D and 7E show five-point ellipsometry thickness uniformity test reports, showing 10 nm+/−1 nm thick alumina films on silicon via a standard ALD deposition protocol.

When depositing thin films via atomic layer deposition (<10 nm), it is often important to consider the substrate surface properties. Particularly in the case of ALD on polymers, surface roughness can be attributed to the initial ALD cycles diffusing into the polymer material (15 to 30 cycles) before reaching self-limiting, layer-by-layer growth.

Beyond a critical number of cycles, the ALD material eventually acts as a diffusive barrier into the polymer and sequential growth may proceed. The mechanism for ALD nucleation/growth on polymers, as indicated by literature, is illustrated in FIGS. 8A-8D.

From experimental observations, impedance spectroscopy, and SEM, the actual deposition thickness is believed to range somewhere between 15 to 30 nm, approximately corresponding with 10 nm of deposition on silicon wafer measured via ellipsometry (see, e.g., FIG. 8E). The discrepancy between these thickness estimates may be rationalized through consideration of the mechanism illustrated in FIGS. 8A-8E; the diffusive front of TMA precursors during the initial nucleation phase may effectively add to the desired 10 nm deposition to be expected if there were already a diffusive barrier on the polymer. SEM on high-aspect ratio, insulative materials often comes with artifacts in the form of sputter material thickness and surface charging from the electron beam. This is to say, SEM estimates of ALD thickness should be understood qualitatively.

Biological surface interactions occur predominantly on the outer wall of nanostraws. There is evidence to support a strong correlation between cell adhesion and surface roughness, and our models indicate surface roughness from the ALD process may be actually be beneficial for nanostraw-cell penetration. This is consistent with observations of spatially uniform device transfection efficiencies within batches.

As mentioned above, nanostraws have previously been described, and optimized, from alumina. Surprisingly, it has been found that nanostraws having desirable properties may be formed of other materials, including silica or hafnia ($HfO_2$). These materials may be more easily scaled, and may also provide improved performance, both for cell viability in culture and also for transfection efficiency.

Silica ($SiO_2$) nanostraws were anticipated to perform well in terms of both TE and CV due to silica's observed biocompatibility and surface chemistry. Surprisingly, although the biocompatibility of such straws was high, the transfection efficiency was remarkably low. The silica crystal structure can readily be functionalized to direct cell compatibility via silane chemistry. Further, the isoelectric point, or the pH at which the surface charge of the material in aqueous solution is neutral, is significantly lower than that of alumina (~2-3 vs~8-9).

It may be expected that the isoelectric points of the nanostraw material may be related to the properties of the material when operating as a nanostraw because solution conditions for nanostraw-mediated delivery must be biocompatible, i.e. buffered at pH~7, and should not capture (or prove "sticky") for even charged materials being passed into the cells through the straws. The silica surface may be negative charged whereas alumina surface would be positive with respect to the bulk solution. In the case of alumina, a positively charged surface may have unfavorable implications for transport of negatively charged nucleic acids, i.e. plasmid DNA, as this cargo may have a high probability of binding, and clogging within the nanostraw during delivery protocols.

FIG. 9 illustrates an example of a silica nanostraw material. Silica nanostraw fabrication was shown for 100 nm pore size nanostraws. While cell viability on silica architectures was excellent, standard biological protocols for transfection proved less optimal. Silica ALD on polycarbonate also had a reduced compatibility between precursor gas and polymer substrate. The adsorption coverage time was slower for silica on polycarbonate than alumina on polycarbonate. This difference in adsorption time may be attributed to a higher activation barrier for silica precursor adsorbed to polycarbonate than aluminum precursor adsorbed to polycarbonate. To account for this adsorption barrier, while not breaching the melting point of polycarbonate (~150 degrees C.), the silica atomic layer deposition was plasma enhanced to better suit the redox surface chemistry. The precursors TDMAS, or tris(dimethlyamino)silane, and $H_2O$, were used in the plasma phase at the interface with the substrate for substantial adsorption coverage. Material species in the plasma phase behaved differently than in the gas phase. One challenge with this protocol was enabling the silicon-carrying plasma to reach down into the straws to ensure complete step coverage and conformal coating before proceeding to the next cycle step. This is typically combatted by higher plasma doses to the layer (~104 L). $SiO_2$ ALD on polycarbonate for nanostraw devices has been demonstrated in an ALD window of 60-100 degrees Celsius. However, the link between higher plasma doses and the atomic scale surface roughness of the silica layer has yet to be fully explored in the context of preserving polycarbonate membrane quality during processing.

Surprisingly, hafnia ($HfO_2$) nanostraws were found to be advantageous, even as unexpectedly compared with Alumina. Low temperature hafnia ($HfO_2$) ALD parameters for PCTE membranes are similar to alumina parameters. Hafnia precursors, tetrakis (diethlyamino) hafnium (TDEAH) and $H_2O$, may be thermally enhanced as previously described for alumina nanostraws. For example, the Savannah 200 ALD system (see FIG. 7A, above) may be used in a similar manner. However, the use of hafnia nanostraws of comparable size to alumina straws had a higher TE. This may be because the isoelectric point of hafnia is approximately 7, so that in aqueous solution the surface chemistry may be predominantly neutral during delivery. A neutral surface chemistry would not attract charged molecules in solution; hence, the likelihood of clogging cargo would be low.

Hafnia may be reactive ion etched via fluorine-based etched chemistry ($CF_4$) in addition to chlorine-based etch chemistry ($BCl_3$) as with the case of alumina (discussed above). The advantage with fluorine chemistry lies in the relative ease of regulation and maintenance compared to the cost, labor, and risk associated with maintaining chlorine-based etch chemistries.

Figure 10:
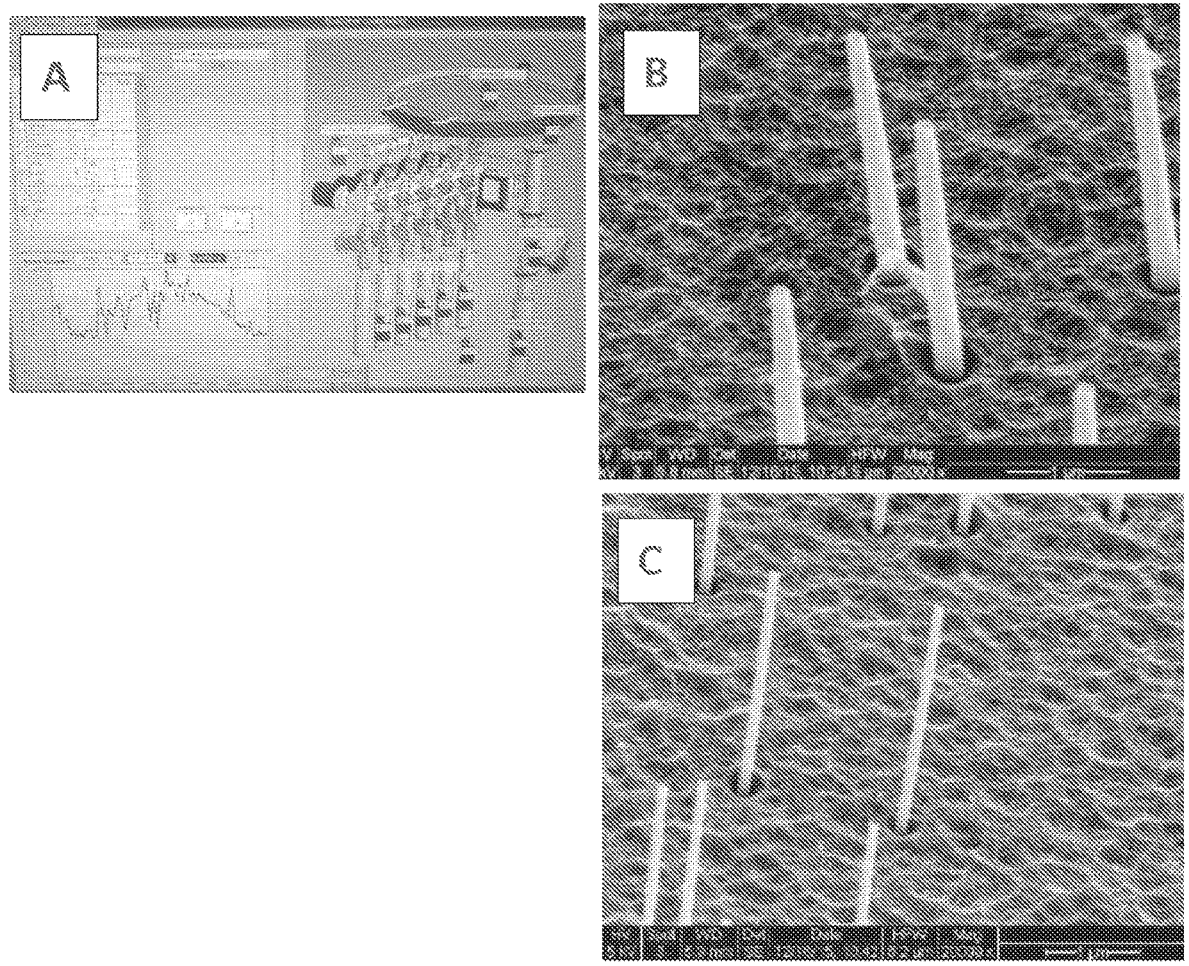
FIGS. 10A-10C show the fabrication and characterization of hafnia nanostraws.

FIG. 10 illustrates hafnia nanostraws. As shown in FIG. 10A, the hafnia nanostraws were successfully fabricated using a Savannah 200 (Cambridge Nanotech) utilizing similar processing parameters as alumina-based nanostraws. In FIG. 10B, hafnia nanostraws exhibit clean, open pores and appear to have uniform diameters along the entirety of the straw length, also shown in FIG. 10C. Hafnia offers the advantages of low-temperature deposition, a relatively neutral isoelectric point, and potential compatibility with fluorine-based etch chemistries.

Nanostraw production may be scaled to higher throughputs, despite the relatively slow ALD rates. The deposition rate in thermally enhanced ALD reactors can be significantly increased by moving from the time-limiting domain to the spatial domain for the dosing of the various process gases in parallel as well as over large substrate areas. Throughputs as high as 3600 ALD coated wafers/hour have been reported. In addition, the use of flexible polymer substrates may allow ALD coating into roll-to-roll processing.

Any of the nanostraws described herein may be formed using an anisotropic dry etching process to etch the top metal oxide layer when forming the nanostraws. For example, dry etching techniques can generate anisotropic etch profiles and have come into favor in recent years for reasons of selectivity and directionality. Etching processes have been generally can be grouped classified into five categories: sputter etching, chemical etching or gasificaiton, accelerated ion-assisted etching, sidewall-protected ion-enhanced etching, and reactive-ion etching.

The term reactive-ion etching has often been used to refer to anisotropic etching; however, this is not entirely correct. In low-density plasmas, i.e. with current densities 0.01 to 1 $mA/cm^2$, there are too few impinging ions to achieve practical etch rates. However, in the more recent high-density plasma-etching systems bombarding ion fluxes, with current densities of 1 to 10 mA/cm2, a sufficient concentration of "hungry ions" may be created to devour substrates. It is for such cases that the term reaction-ion etching is appropriate.

One of the important considerations in plasma etching is the temperature rise in the film/substrate. Plasma-etching species and sputtered atoms that imping on surfaces are far more energetic, for example, than comparable atoms emanating from evaporation sources. During ionic impact, condensation, and reaction, the excess energy liberated must be dissipated via the substrate (as heat dissipation in vacuum is radiative) or otherwise it may heat excessively to the detriment of film quality.

The etching or removal of atoms from film or substrate surfaces that are immersed in plasmas occurs by both physical and chemical means. Changing the ion energies and pressures shifts the dominant material-removal processes. For example, physical sputter etching occurs at the lowest pressures (~1 mtorr) and highest energies (keV). Ion-assisted etching via the surface damage mechanism takes place at lower energies and somewhat higher pressures (~50 mtorr). In both cases surface etching tends to be anisotropic. However, with chemical etching at elevated pressures of ~1 torr, energetic ion bombardment is precluded and the result is isotropic attack of films. Because the mass of many of the ionic species in practical plasma etching processes is large, their motion may not be in phase with the RF field. As a result, the ionic-displacement amplitude and energy are generally too low to cause sputtering.

In the PlasmaQuest ECR etcher, a plasma is created by the electron-cyclotron resonance effect. The microwaves are tuned to the cyclotron resonance frequency of electrons in the gas. They excite the atomic electrons to the point where they gain enough kinetic energy to be stripped off of the atoms, ionizing the gas. This allows plasma to be created without an electrical discharge and without increasing the temperature of the ions in the plasma by a significant degree. The resulting plasma can thus have a low temperature and a low density, and also has a high ionic fraction, which may be useful for plasma etching on polymer substrates, including plasma etching to form the nanostraws described herein.

Fabrication of the nanostraws described herein typically includes oxidation. Electrons, produced by ionization of gas (e.g., 10% $O_2$, 90% Ar), gain energy in the electric field. Subsequent collisions between these energetic electrons and neutral gas molecules result in an energy transfer to the molecules producing chemically active atoms, free radicals, ions and free electrons. The combustion products, which are dissociated and harmless, are carried away in the gas stream outlet. This process occurs near ambient temperatures without employing toxic chemicals and it is highly selective to polymers over metal oxide structures such as alumina, silica, and hafnia.

Provided the mechanism of plasma oxidation, characteristics, i.e. etch rate, selectivity, roughness, etc., may be a function of plasma characteristics such as RF power (W), chamber pressure (mTorr), gaseous partial pressures (mTorr), chamber temperature, and substrate temperature.

Standard etch protocols include four sequential etch cycles which may yield 1.0 to 1.5 nanostraw length (factoring in 30 to 45 degree viewing angle). No clear differential trend in performance has been internally observed, to date, across this nanostraw length range.

Nanostraw well inserts may be fabricated or assembled using any of the nanostraws described herein. For example, FIGS. 11A-11D illustrate one example of nanostraw assembled using the improved methods described herein. In FIG. 11A, components for a nanostraw well insert apparatus are show, including a double-sided annular tape 1101, a polycarbonate (PC) tube 1103 and the nanostraw membrane 1105. Device assembly entails cutting or forming the PC tube, and cutting or forming the double sided tape to the respective dimensions. In FIG. 11B, the double-sided tape may be mated with the tube, and then sticking the tube to the nanostraw membrane (oriented with the nanostraws facing into the tube). Optionally, as shown in FIG. 11C, the excess material 1105' may be trimmed. FIG. 11D illustrates a nanostraws well insert devices integrated into an existing culture well plate 1107. Thus, the assembly of nanostraw well inserts may include: taping one side of the double-sided annular tape to one end of a polycarbonate tube-well; taping the opposite side of the double-sided tape to the nanostraw membrane (nanostraws normal to device); and optionally cutting and trimming excess nanostraw membrane from edges of nanostraw well insert using standard trimming tools.

Following assembly, the nanostraw well insert devices may be cleaned with 70% ethanol in water, air dried for 10 to 15 minutes, and sterilized in UV light for 15 minutes. Nanostraw well inserts may fit readily into existing 6-, 12- and 24-well plates, and are imaging friendly.

The cutting/trimming process may be batch performed at-scale with metal die cutters, or with $CO_2$ laser welding directly to polycarbonate tube-wells. Further, the dimensions of the tube wells may likely be designed taking into account ergonomic considerations.

Any of the apparatuses, including any of the nanostraw well insert devices described herein may be used for cell culture, and particularly long-term cell culture (e.g., longer than five days), and used at any time to access the internal structure of the cell (e.g., to transfect material into the cell. Unlike previously described and characterized nanostraw devices, these apparatuses may be used for longer than 5 days, including up to at least 3 weeks, without significantly effecting cell viability; further, at any time during this period the nanostraw structures may be used to access (e.g., deliver material, remove material, etc.) internal cell materials.

Figure 12:
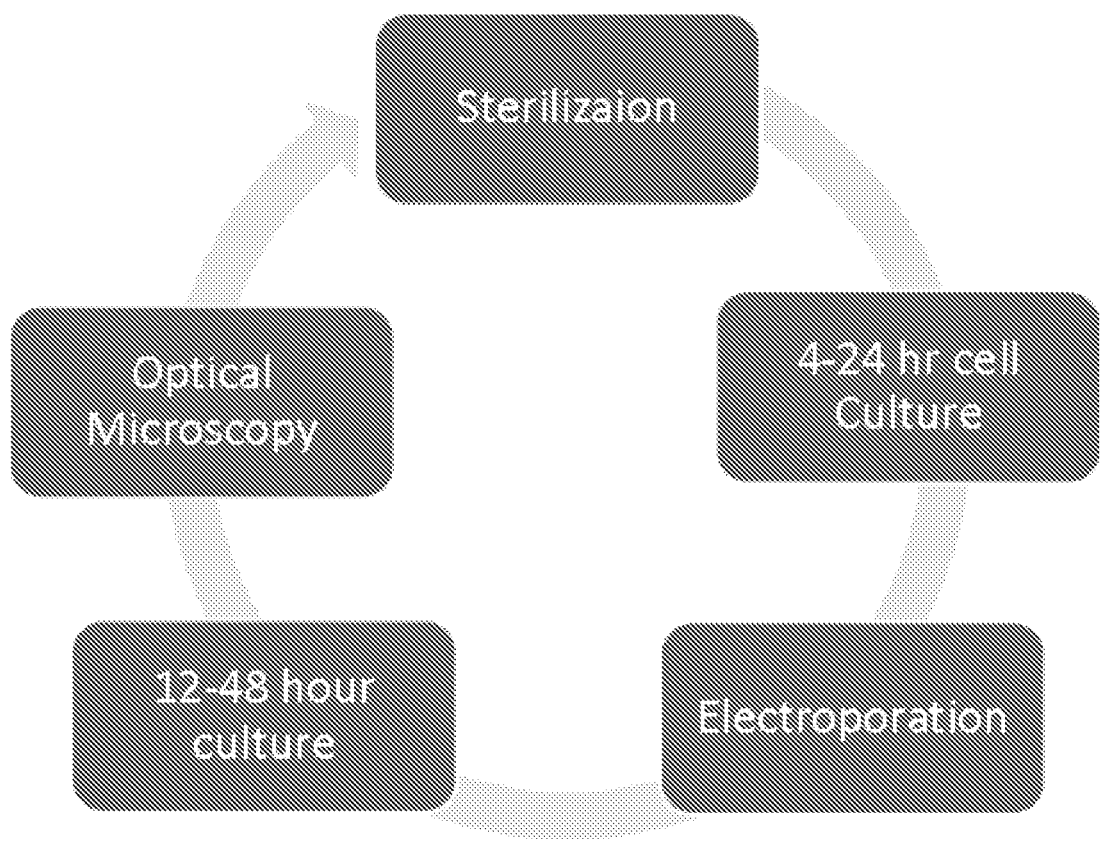
FIG. 12 illustrates an example of a standard transfection protocol for expression of nucleic acid delivery into model cell lines. In this example, the method typically takes 24 to 72 hours from sterilization to image analysis, depending on whether or not translocation is required for expression. Transfection steps include sterilization, cell culture, electroporation, cell incubation, and optical microscopy.

For example, FIG. 12 illustrates a short-term prior standard cell culturing protocol for a model cell line (e.g., such as CHO, HEK293T, HeLa, etc.). After assembly, a nanostraw well insert device may be sterilized, e.g., with 70% ethanol in water, air dried for 10 to 15 min and placed under UV light ($\lambda$=305 nm) for 15 min. Generally speaking, a standard protocol may entail culturing cells on top of the nanostraw membrane for over 4 hours (typically, an overnight culture) in 350 µl of "regular" media (e.g., 10% Fetal bovine serum (FBS), DMEM media from Invitrogen company (Cat #10564) plus 1× Penicillin/Streptomycin (P/S)). A nanostraw well insert apparatus may be placed in a 24-well plate containing a bath of 350 µl of 1× regular media (dispensed external to the nanostraw device). After electroporation/transfection, cells are cultured for an additional 12-48 hours prior to analysis via optical microscopy.

Figure 13:
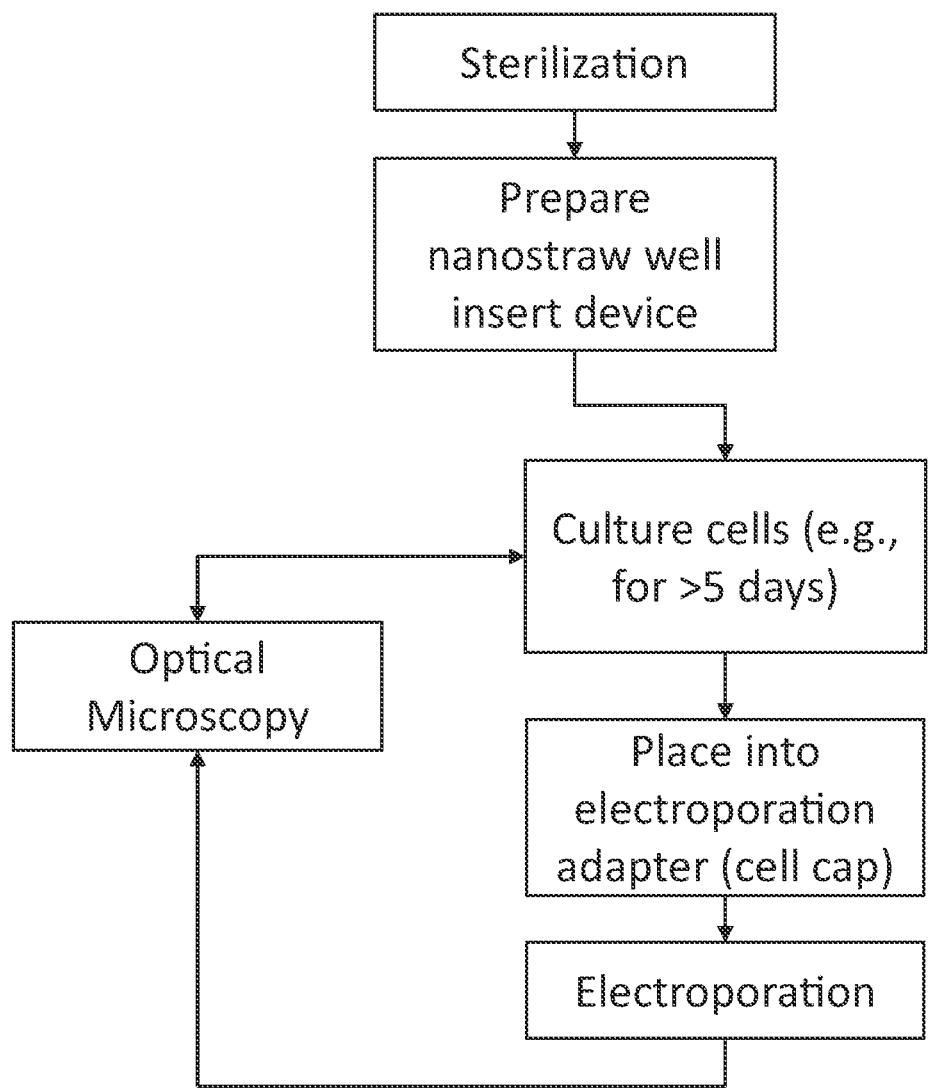
FIG. 13 illustrates a longer method of cell culture and transfection (e.g., taking longer than 5 days, including culturing in the improved nanostraw well insert apparatuses described herein.

Because the apparatuses, including formed as described herein have been shown to have particularly long viability time periods (e.g., exceeding five days) for tissue culture, particularly as compared to those previously described, including in particular alumina nanostraws, cells may be cultured for an extended period of time. For example, FIG. 13 illustrates one method for using the nanostraw well insert apparatuses described herein. In FIG. 13, the insert is first sterilized, and may then be prepared for cell culture. For example, the cell culture medium may be added to the inside of the insert device, and the insert may be placed into a tradition multi-well dish, for which it is well adapted. Additional cell culture medium (the same or a different medium) may be added to the dish into which the insert is placed, and a cover provided. Cells may also be added into the insert device. Thereafter, the cells may be incubated for a desired period of time, including in particular very long times (>5 days). This is in contrast to prior variations of the nanostraw devices, for which cell viability dropped dramatically after 3-4 days (e.g., with less than half of the cells surviving beyond this period. The apparatuses described herein may have>50% (e.g., >60%, >70%, etc.) viability after 5 days.

In addition to being well adapted for use with a multi-well dish, as discussed above, the nanostraw well insert devices described herein may be adapted specifically for use with an electroporation adapter that may securely hold the nanostraw well insert device. Electroporation adapters (also referred to herein as "cell caps") are described in greater detail below, and may generally have a cylindrical body into which the insert device may be inserted and held above a cargo region calibrated so that the bottom of the nanostraw well insert device does is separated from a base electrode by a predetermined distance that is also configured to prevent bubbles/vapor formation between the base electrode and the bottom of the insert device. A cap portion may then be placed over the cylindrical body so that a second (top) electrode is held a fixed, predetermined distance from the bottom electrode, and projects into the insert device. The walls of the electroporation adapter (cell cap) may be insulated (e.g., thermally insulated, electrical insulated, etc.). The cap may also seal the apparatus so that it may be transported (e.g., to an electroporation apparatus), and may include external contacts in communication with the top electrode and base electrode, so that electroporation may be performed from outside of the apparatus, controllably transporting a cargo (e.g. plasmid, protein, etc.) from the cargo solution region above the base electrode, though the nanostraws, and into the cells.

To optimize the nanostraw well insert devices and the electroporation adapters (cell cap), factors believed to affect transfection efficiency (TE) and cell viability (CV) were quantified. Among these tested factors were: confluency, top electrode geometry, electrode-electrode distance, applied voltage and stimulus duration, osmolarity in the top solution, and washing media before electroporation. Confluency was tested from 25,000 cells to 200,000 cells with the best TE and CV with 25,000 cells.

The electrode distance was observed to play a critical role with respect to the field strength delivered to cells on Nanostraw devices. Distances of 0.25 cm to 1.25 cm were examined with 0.5 cm showing relatively higher TE and CV. TE and CV were inversely related with increasing field strengths (i.e., shorter electrode-electrode distance, higher applied voltage, and longer stimulation duration). Model cells lines survived up to 15V of applied voltage with greater than 80% CV; however, cell death increased rapidly above this threshold voltage. Electrode geometry was not observed to have a significant contribution to performance amongst planar, point, and spiral designs. Exchanging for fresh media directly before electroporation with a solution of lower osmolarity (PBS vs "regular" media) indicated healthier cells and higher transfection rates.

Thus, in some variations, the use of electrodes built into the nanostraw well insert devices and/o the electroporation adapters may be important in enhancing both TE and CV. For example, separation between the top electrode and the base electrode (with the nanostraw substrate between the two, shout optimally be between 0.25 cm to 1.25 cm, e.g., between 0.3 cm and 0.8 cm when the voltage applied is <15 V. Outside of this range (e.g., >1.25 cm), cell viability, particularly for longer culture times, fell off sharply.

As an example, an electroporation transfection protocol using nucleic acids in model cell lines was used to examine the apparatuses described herein. Prior to each transfection via electroporation, the bottom Pt electrode (base electrode) was cleaned with 70% ethanol to water using a standard Kimwipe. 60 µl of liquid delivery precursor (e.g., the cargo solution, such as nucleic acid, plasmid, protein, fluorescent dye, $Co^{+2}$, etc.) was dropped into the delivery reservoir (see FIG. 2A). The pre-cultured nanostraw well device may be placed into a delivery precursor holder (e.g., an electroporation adapter/cell cap) and slight pressure may be applied to ensure complete wetting of the liquid delivery precursor to the bottom of the nanostraw membrane. The top Pt electrode was then lowered into the nanostraw well device solution at approximately 0.7 cm above the bottom Pt electrode. From past observation, it is important to allow 1 minute prior to applying electricity. This is to ensure complete wetting of the nanostraws membrane with delivery precursor via simple diffusion.

After allowing time for diffusion, DC electricity was applied across the nanostraw well device (e.g., across the electroporation holder/cell cap). The standard electrode configuration is negative and positive for the bottom and top electrodes, respectively. Negatively charged precursor may be electrically driven upwards into the top solution and cell culture. The standard DC pulse profile is as follows: voltage of 10 V, individual pulse width of 200 µs, frequency of 20 Hz, total time duration of 40 seconds. After pulsing electricity, the nanostraw well device should remain in contact with the delivery precursor for an additional minute to allow for diffusion of species into opened electropores. The device is then placed back in the incubator for an additional 12 to 48 hours prior to imaging.

Figure 14:
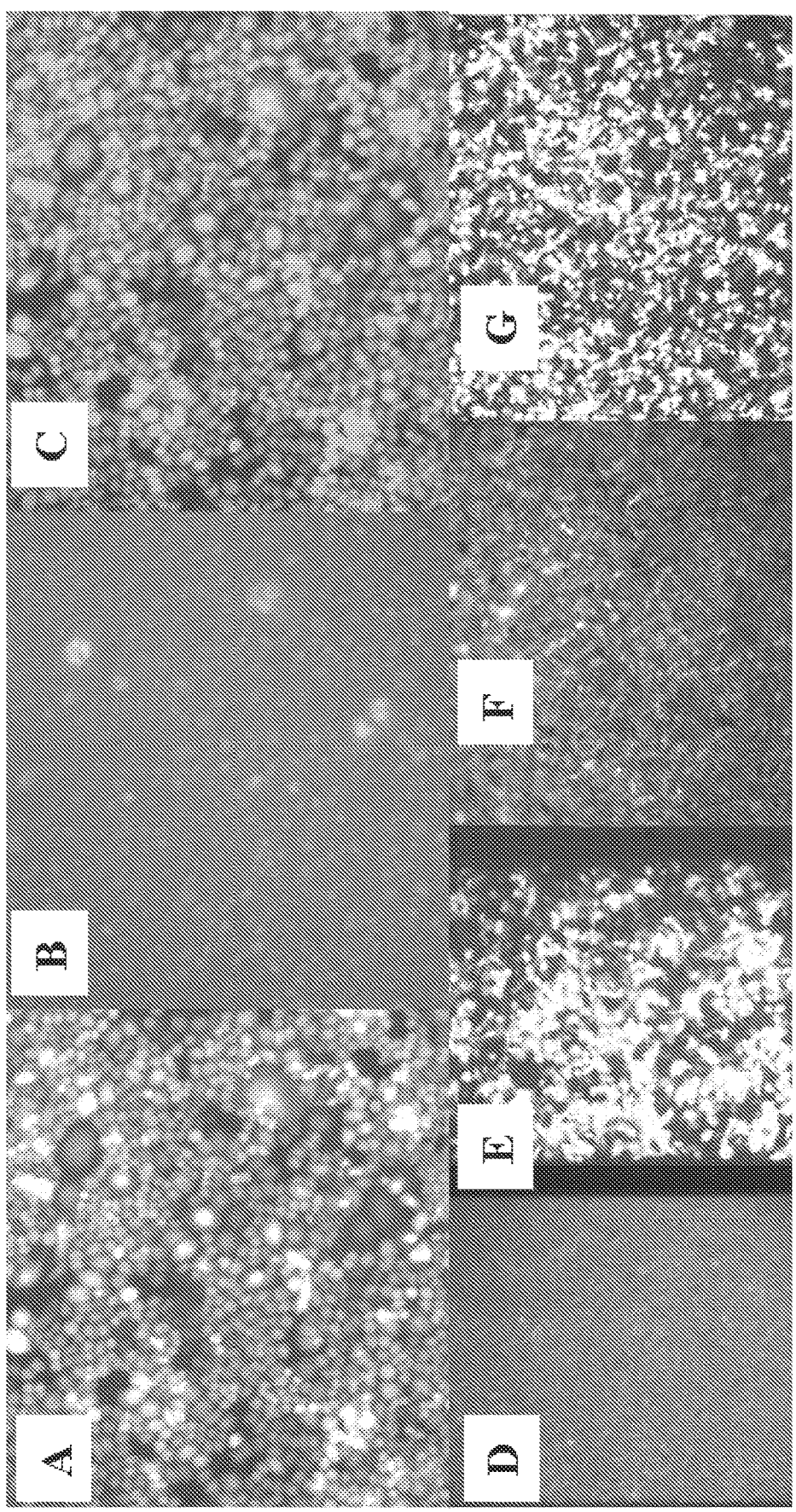
FIGS. 14A-14G illustrate delivery of nucleic acids into model cell lines using the apparatuses and methods described herein.

FIGS. 14A-14F illustrate delivery of nucleic acids into model cell lines can be enhanced via fabrication and experimentation parameter optimization as discussed above. In FIG. 14A, oligonucleotide delivery is shown into green-fluorescing HeLa cells (green channel florescence is used to indicate HeLa cell confluency. In FIG. 14B, a red channel is used for imaging to indicate red dye transfection, In FIG. 14C, showing merged green and red channels to quantify transfection efficiency. In this example, TE>90%; this high TE result was reproducible and quite efficient using the nanostraw well insert platform described above. Plasmid delivery into HEK 293T cells green-fluorescing CHO cells was also examined. In this example, pEGFP delivery into HEK 293T model cell line exhibited>75% efficiency. In FIG. 14D a blue channel was used to image Hoeschst staining for cell identification; in FIG. 14E a green channel was used for imaging pEGFP expression and fluorescence for quantifying TE. Further, the standard transfection protocol with pmCherry delivery into green fluorescing CHO cells yields>75% TE (shown in FIG. 14F, showing a green channel for CHO cell identification and FIG. 14G, showing a red channel for pmCherry plasmid expression and fluorescence for TE quantification). All optical images were taken at the same exposure (200 ms), respectively, and imaged at multiple magnifications (FIGS. 14A-14C at 20× magnification; FIGS. 14D-14G at 10× magnification).

Figure 1A:
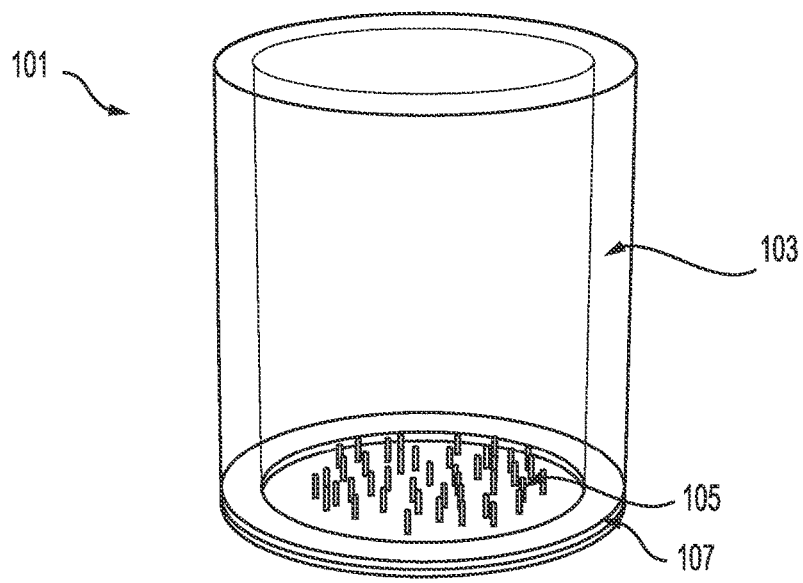
FIG. 1A schematically illustrates one example of a nanostraw well insert.
Figure 1B:
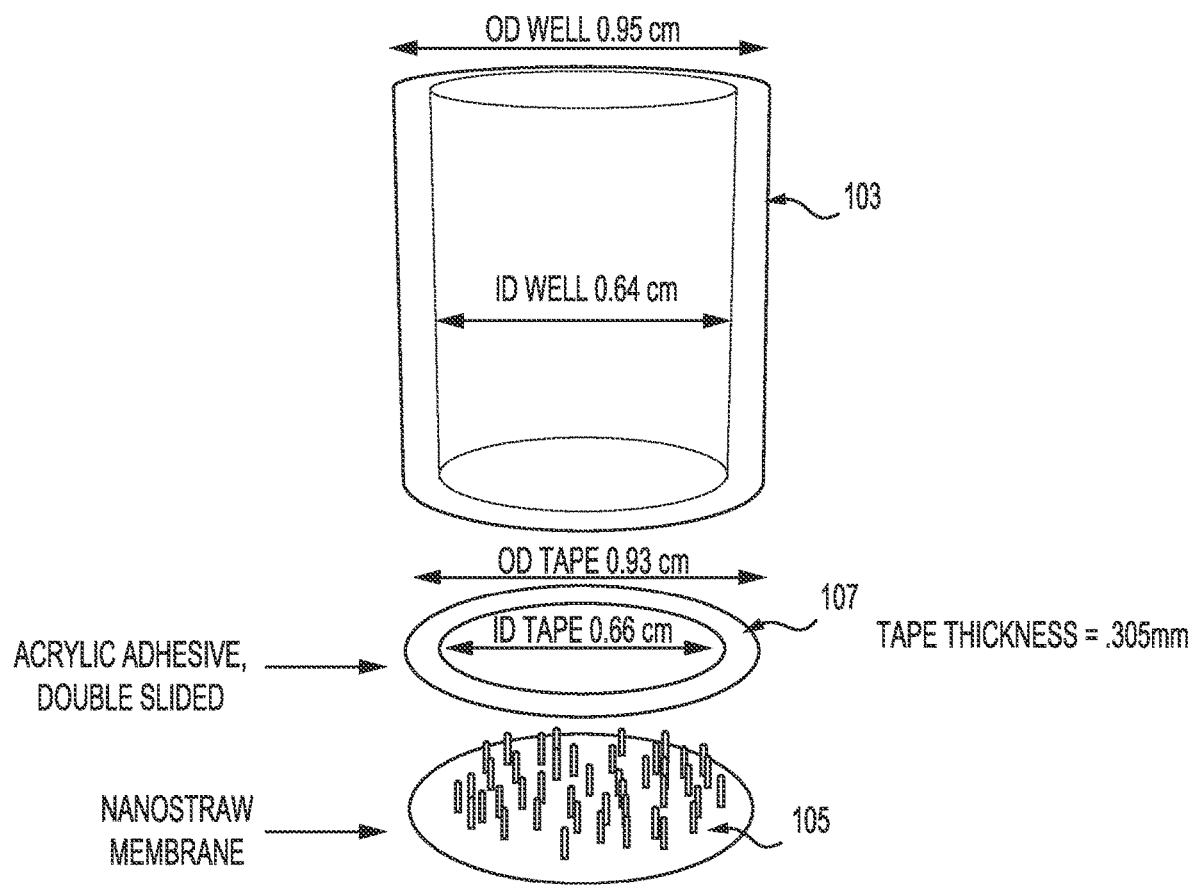
FIG. 1B shows an exploded view of this insert, with exemplary dimensions shown.

Returning now to FIGS. 1A-1B, showing a nanostraw well insert device 101. In this example, the nanostraw well insert device includes a cylindrical body 103 formed of an inert, preferably clear, material, such as polycarbonate. The nanostraw-containing substrate 105 is attached over the bottom of the cylinder by a double-sided tape 107, forming a well into which cells may be grown. The nanostraw material may, in particular, be nanostraws formed of a material such as hafnia. FIG. 1B is an exploded view of the nanostraw well insert device 101, showing exemplary dimensions for the cylindrical body 103, double-sided tape 107, and nanostraw membraned 105.

Figure 2A:
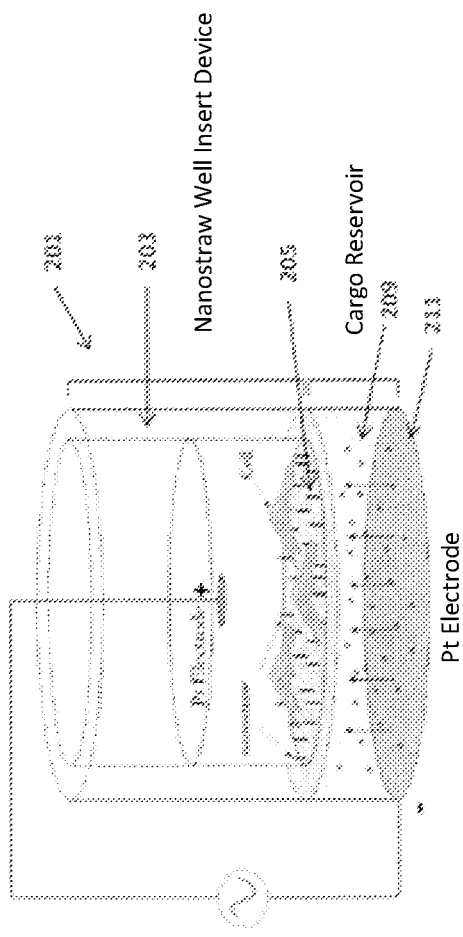
FIG. 2A shows another schematic illustration of a nanostraw well insert for culturing and testing cells.

FIGS. 2A-2D illustrate another example of a nanostraw well insert apparatus. In FIG. 2A, a generic nanostraw well insert device is show during transfection. The insert device may be used with a matching delivery precursor holder (e.g., an electroporation adapter/cell cap), as mentioned. In FIG. 2A, the inset portion of the apparatus consists of a polycarbonate tube 203 with a nanostraw membrane 205 attached to the bottom so as to make a culture well, as described in reference to FIG. 1A-1B, above. Cells may be cultured directly in the device well with media (the upper media is "regular media," as described above in the transfection protocol). The insert apparatus may be nitrated into a delivery precursor holder (e.g., an electroporation adapter/cell cap) or the holder/adapter may be separate. In FIG. 2A, for transfection via electroporation, the insert is placed into contact with a cargo reservoir 209 containing the molecular species to be delivered (shown here as small spheres in solution; e.g., typically, DNA/RNA in water). The cargo reservoir may be formed in the holder/adapter and may be configured to prevent bubbles forming between the base electrode 211 and the bottom of the membrane of the insert, as this may deleteriously affect transfection.

Electric pulses may be fired between the top electrode and the bas electrode, which are shown in this example as platinum electrodes; this may open pores in the cell membrane, enabling intracellular access through the nanostraws.

Figure 2D:
FIGS. 2C and 2D illustrate false-colored SEM images of cryo-fixed CHO cell on nanostraw membrane to illustrate the practical device principle. Nanostraws such as these have been demonstrated to spontaneously penetrate the cell membrane, and the applied electrical pulses may enhance delivery efficiency.
Figure 2C:
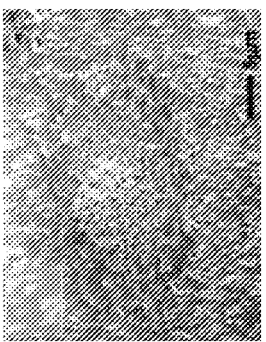
Figure 2B:
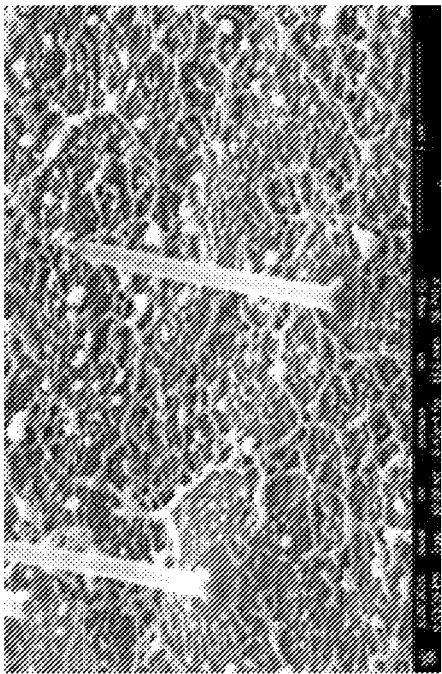
FIG. 2B shows nanostraw imaged via scanning electron microscopy; straw length typically ranges from 1 to 3 microns and the outer diameter is on the order of 100 nm.

FIGS. 2A-2D show scanning electron microscopy (SEM) of nanostraws that may form part of the nanostraw membrane, including cells growing on them. In this example, the straw length typically ranges from 1 to 3 microns and the outer diameter is on the order of 100 nm. In FIG. 2C-2D, the SEM image shows a cryo-fixed CHO cell on nanostraw membrane to illustrate the practical device principle. Nanostraws have been demonstrated to spontaneously penetrate the cell membrane and electrical pulses act as "valves" to enhance delivery efficiency.

Figure 15A:
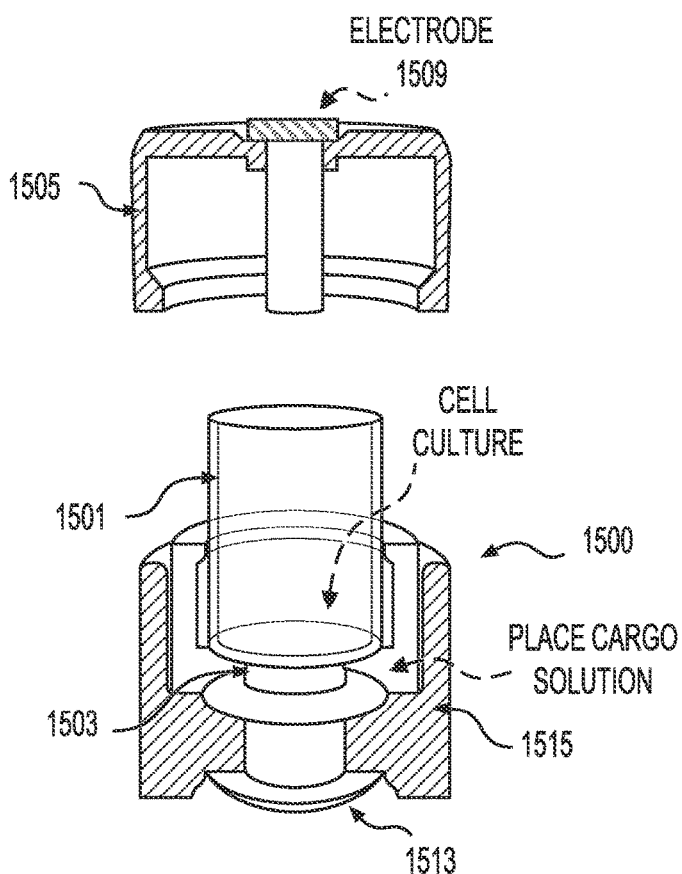
FIG. 15A shows an example of an apparatus including a nanostraw well insert and an electroporation adapter or carrier.
Figure 15B:
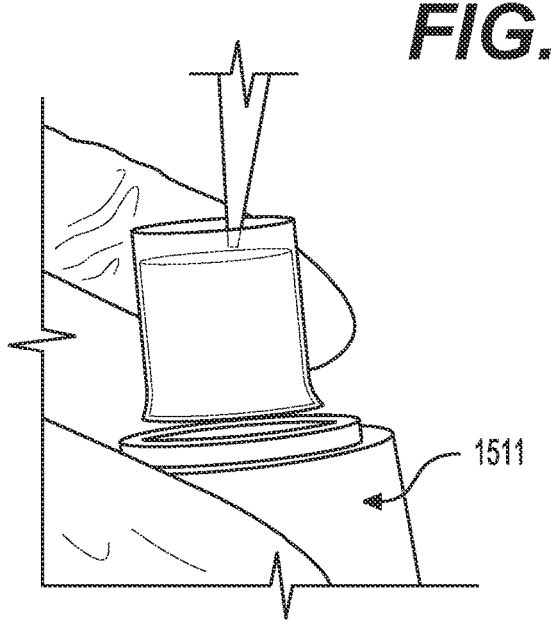
FIG. 15B shows a well insert being inserted into the base of an adapter/carrier.
Figure 15C:
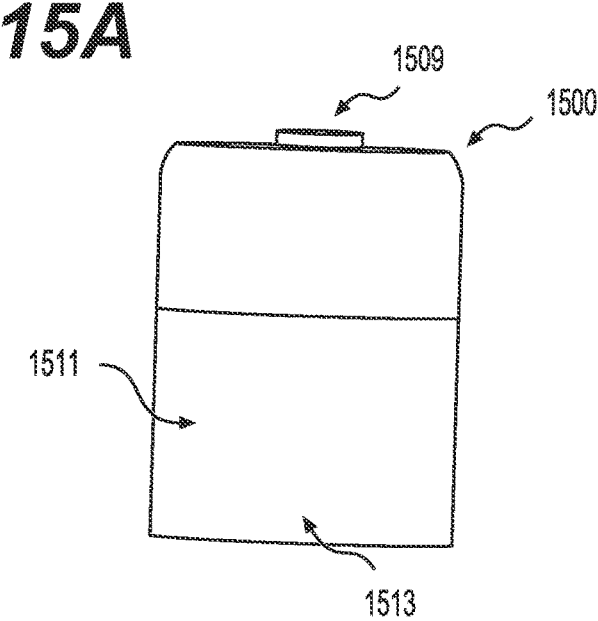
FIG. 15C shows the closed adapter/carrier holding a nanostraw well insert onto which cells have been cultured. The adapter/carrier and enclosed nanostraw well insert may be held and manipulated while protecting the cultured cells, including placing into an electroporation apparatus for delivery of electrical current.

Turning now to FIG. 15A-15C, an apparatus including a nanostraw well insert device and a compatible/matching delivery precursor holder (e.g., an electroporation adapter/cell cap) are shown. FIG. 15A shows a nanostraw well insert 1501 inserted into a holder (also referred to as an electroporation adapter or cell cap 1500. The nanostraw well insert is substantially as described above in FIGS. 1A-1B and 2A. The electroporation adapter is configured to secure the insert within an elongate cylindrical body 1515, so that the bottom of the insert is flat and parallel with the base electrode 1513.

The base electrode is secured across the bottom of the adapter and may be flat or concave, to hold and form the reservoir depot 1503. As mentioned, the adapter may be configured to prevent bubbles from getting trapped between the membrane of the nanostraw well insert and the base electrode; for example, the adapter may include one or more channels in the side and/or through the side to allow air to escape from between the flat bottom of the membrane in the insert and the depot 1503.

In general, the electroporation adapter is configured to hold the insert securely, within the cylindrical chamber, and a cap 1505 including a top electrode 1509 may be attached over the insert when it is held within the device. The cap may be held on and in place by a friction fit and/or a mechanical, magnetic, or other attachment (e.g., screwed on, snapped on, etc.). The cap my in particular, hold the top electrode in position over and at least partially into the insert. The entire electroporation adapter may maintain the separation between the top electrode and the base electrode as optimally described here (e.g. between 0.3 and 0.8 cm, or about 0.5 cm).

The top electrode 1509 and base electrode 1513 may be positioned within the adapter as shown, but may include one or more connections to electrical contacts on the outside of the adapter so that even as the insert is held within the sterile internal chamber of the adapter, the entire apparatus may be manually held and manipulated, including placing into an electroporation apparatus for applying current across the electrodes as described above.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A nanostraw cell culture system for long-term cell growth and transfection, the system comprising:
   a nanostraw well insert device comprising a cylindrical wall, a membrane from which a plurality of nanostraws project; and a biocompatible adhesive connecting the membrane across a base of the cylindrical wall to form a well, wherein the nanostraws project into the well greater than 0.1 microns; and
   an adapter configured to hold the nanostraw well insert device, the adapter comprising:
   a base comprising a base electrode, wherein the based is configured to securely hold the cylindrical wall of the nanostraw well insert device so that the plurality of nanostraws are in fluid communication with a reservoir depot over the base electrode;

a cover comprising a top electrode, wherein the cover is configured to engage the base so that when a nanostraw well insert device is held within the base, the top electrode is separated from the base electrode with the nanostraw insert device enclosed there between;

a first electrical contact on an outer surface of the adapter, wherein the first electrical contact is in electrical communication with the base electrode; and a second electrical contact on the outer surface of the adapter, wherein the second electrical contact is in electrical communication with the top electrode.

2. The system of claim 1, wherein the base is configured to vent air between the reservoir depot a bottom of the nanostraw well insert.

3. The system of claim 1, wherein the adapter further comprises an inlet configured to regulate the pressure of the reservoir depot in the base.

4. The system of claim 1, wherein the first electrical contact is on a top of the cover and the second electrical contact is on a bottom of the base.

5. The system of claim 1, wherein, when the cover is engaged with the base, the top electrode is separated from the base electrode by between 0.25 cm and 1.25 cm.

6. The system of claim 1, wherein the reservoir depot includes a concave surface on the base electrode.

7. The system of claim 1, wherein the base comprises a cylindrical housing.

8. The system of claim 1, wherein the cover is configured to secure over the base so that the nanostraw well insert device is completely enclosed therein.

9. A nanostraw well insert device for long-term cell growth a transfection, the device comprising:

a cylindrical wall;

a membrane through which a plurality of hafnia ($HfO_2$) nanostraws project; and a biocompatible adhesive connecting the membrane across a base of the cylindrical wall to form a well, wherein the nanostraws project into the well for greater than 0.1 microns.

10. The device of claim 9, wherein the cylindrical wall has a round transverse cross-section.

11. The device of claim 9, wherein the cylindrical wall comprises one of: a polycarbonate tube, an acrylic tube, a polycarbonate tube, or a polyethylene terephthalate (PET) tube.

12. The device of claim 9, further comprising an adhesive between the cylindrical wall and the membrane.

13. The device of claim 9, further comprising an acrylic adhesive between the cylindrical wall and the membrane.

14. The device of claim 9, wherein the plurality of hafnia nanostraws have a pore size of between 10 nm and 1000 nm.

15. The device of claim 9, wherein the plurality of hafnia nanostraws project into the well between 0.1 and 25 microns.

16. The device of claim 9, wherein the plurality of nanostraws each comprise a continuous channel extending from outside of the device, through the membrane and into the well.

17. The device of claim 9, wherein an outer diameter of the cylindrical wall is between 1.5 cm and 0.5 cm.

18. A method of culturing and transfecting cells, the method comprising:

culturing one or more cells in a nanostraw well insert device, wherein the nanostraw well insert device comprises a cylindrical wall and a membrane extending across a base of the cylindrical wall to form a well, wherein a plurality of nanostraws project through the membrane and into the well greater than 0.1 microns;

placing the nanostraw well insert device into a base of an adapter so that the plurality of nanostraws are in fluid communication with a reservoir depot in the base, wherein the reservoir depot is in electrical communication with a base electrode in the base;

placing a cover over the base, wherein the cover comprises a top electrode, so that the top electrode extends into the nanostraw well insert device and the top electrode is separated from the base electrode with the nanostraw well insert therebetween;

applying a voltage between the base electrode and the top electrode to deliver a material from the reservoir depot, through the plurality of nanostraws and into the one or more cells; and removing the nanostraw well insert from the adapter and culturing the one or more cells in the nanostraw well insert.

19. The method of claim 18, wherein placing comprises pacing the cover over the base so that the top electrode is separated from the base electrode by between 0.25 and 1.25 cm.

20. The method of claim 18, wherein applying the voltage comprises applying the voltage between a first electrical contact on an outside surface of the adapter and a second electrical contact on an outside of surface of the adapter, wherein the first electrical contact is in electrical communication with the top electrode inside the adapter and the second electrical contact is in electrical communication with the base electrode inside the adapter.

21. The method of claim 18, wherein applying the voltage comprises applying between about 0.1 V and 20 V.

22. The method of claim 18, wherein applying the voltage comprises applying less than 15V.

23. The method of claim 18, further comprising imaging the cell in the nanostraw well insert device.

24. The method of claim 18, wherein applying the voltage comprises applying a pulse width of between 10 and 500 microseconds at a pulse frequency of between 1 Hz and 10 kHz.

25. The method of claim 18, wherein culturing the cell comprises culturing the cells on a plurality of hafnia ($HfO_2$) nanostraws.

26. The method of claim 18, further comprising loading the material into the reservoir depot prior to placing the nanostraw well insert device into the base.

* * * * *